(12) United States Patent
Ludwig et al.

(10) Patent No.: US 6,911,539 B2
(45) Date of Patent: Jun. 28, 2005

(54) POLYMORPHISMS IN A DIACYLGLYCEROL ACYLTRANSFERASE GENE, AND METHODS OF USE THEREOF

(75) Inventors: Erwin H. Ludwig, San Anselmo, CA (US); Robert V. Farese, San Francisco, CA (US); Thomas L. Innerarity, Lafayette, CA (US); Sylvaine Cases, Belmont, CA (US)

(73) Assignee: The Regents of the University of California, Oakland, CA (US)

( * ) Notice: Subject to any disclaimer, the term of this patent is extended or adjusted under 35 U.S.C. 154(b) by 71 days.

(21) Appl. No.: 10/142,516

(22) Filed: May 8, 2002

(65) Prior Publication Data

US 2003/0073103 A1 Apr. 17, 2003

Related U.S. Application Data

(63) Continuation of application No. 09/613,444, filed on Jul. 11, 2000, now Pat. No. 6,444,427.

(51) Int. Cl.[7] .......................... C07H 21/04; C12Q 1/68; C12P 19/34
(52) U.S. Cl. ........................ 536/23.1; 435/6; 435/91.1; 435/91.2; 536/24.3; 536/24.33
(58) Field of Search ........................ 435/6, 91.1, 91.2; 536/23.1, 24.3, 24.33, 23.2, 24.1; 438/780

(56) References Cited

U.S. PATENT DOCUMENTS

| 5,580,730 A | * | 12/1996 | Okamoto | 435/6 |
|---|---|---|---|---|
| 6,100,077 A | * | 8/2000 | Sturley et al. | 435/193 |
| 6,344,548 B1 | | 2/2002 | Farese et al. | |
| 2003/0170691 A1 | * | 9/2003 | Gimeno et al. | 435/6 |

FOREIGN PATENT DOCUMENTS

| WO | WO 9967268 | 12/1999 |
|---|---|---|
| WO | WO00 01713 A | 1/2000 |
| WO | WO 02 36824 A | 5/2002 |

OTHER PUBLICATIONS

Grisart et al., "Genetic and functional confirmation of the causality of the DGAT1 K232A quantitative trait nucleotide in affecting milk yield and composition," PNAS, 2004, fol. 101, No. 8, pp. 2398–2403.*

Accession No. NC_000008, NCBI Sequence Database, 2004.*

"A map of human genome sequence variation containing 1.42 million single nucleotide polymorphisms," Feb. 15, 2001, Nature, vol. 409, pp. 928–933.*

Barsh, et al. "Genetics of body–weight regulation", Nature, (2000) vol. 404: 644–651.

Cases, et al. "Identification of a gene encoding on acyl CoA: Diacylglycerol acyltransferase, a key enzyme in triacylglycerols synthesis", Proc. Natl. Acad. Sci., (1998) vol. 95: 13018–13023.

Chagnon, et al. "The human obesity gene map: The 1999 update", Obesity Research, (2000) vol. 8(1): 89–117.

Robinson, et al. "Genetic models of obesity and energy balance in the mouse", Annu. Rev. Genet., (2000) vol. 34: 687–745.

Smith, et al. "Obesity resistance and multiple mechanisms of triglyceride synthesis in mice lacking Dgat", Nature Genetics, (2000) vol. 25: 87–90.

Chen et al. Trends Cardiovasc Med, vol. 10, No. 5, Jul. 2000, pp. 188–192.

Ludwig et al., "DGAT1 Promoter Polymorphism Associated with Alterations in Body Mass Index, High Density Lipoprotein Levels and Blood Pressure in Turkish Women" Clinical Genetics, vol. 62, No. 1, Jul. 2002, pp. 68–73.

Cases, et al., "Cloning of DGAT2, a Second Mammalian Diacylglycerol Acyltransferase, and Related Family Members", Journal of Biological Chemistry, American Society of Biological Chemists, Baltimore, MD, vol. 276, No. 42, Oct. 2001 pp. 38870–388776.

* cited by examiner

Primary Examiner—Gary Benzion
Assistant Examiner—Young J. Kim
(74) Attorney, Agent, or Firm—Paula A. Borden; Bozicevic, Field & Francis, LLP

(57) ABSTRACT

The present invention provides isolated an polynucleotide comprising a polymorphic nucleotide sequence from a diacylglycerol acyltransferase (DGAT) gene, wherein at least one a polymorphism is associated with a condition relating to DGAT activity. The invention further provides diagnostic assays for detecting the presence in a nucleic acid sample of a polymorphism in a DGAT gene that is associated with a condition relating to DGAT activity, and for detecting a propensity to develop a condition associated with DGAT activity. The invention further provides treatment methods.

13 Claims, 8 Drawing Sheets

```
          10         20         30         40         50
 1234567890 1234567890 1234567890 1234567890 1234567890
 TCTAGAGTCA GAGTCCTCAG TGAACCCTGG CATCCTGAGA TCCAGGATGT    50
 TCTCACTCCA TGCCCTGTGC AATATGCACA CCAAGCCAAG GTGGCCCGCA   100
 ACTGTGGCTG TTACAGTTGA TTAGTTGCTT CATTAACAT  ACAAGATGTC   150
 TGGGCAGTG  GCTCATACCT GTAATCCCAG CACCTTCAGA GGCCGAGGTG   200
 GGAGGATTGC GTGAGGCCAG GAGTTCGAGA CCAGCCTGGG CAGAATAGCG   250
 AGACCCCAT  CTTTAGAAAA AATAACAACA GGCCAGGCGC GGTGGCTTGC   300
 GCCTATAATC CCAGCACTTT GGAGGCCGA  GGTGGGCGGA TCACCACGTC   350
 AGGAGATCGA GACCAGCCTG GCCAATATGG TGAAAGCCCG TCTCTACTAA   400
 AAACAGAAAA ATTAGCTGGG CGTGGTGGCA CGCGCCTGTA GTCCTGGCTA   450
 CTCGGGAGGC TGAGGCAGGA GAATCGCTTG AACCCAGGAG GTGGAGGTTG   500
 CAGTGAGACG AGATCGCGCT ACTGCACTCC AGCTGGGCA  CAGAGTGAGA   550
 CTGTCTCAAA AAAAGAAAAA AGAAAACAAA AACAACAGG  GCGGTTGCAC   600
 AGGCCGTGCA AATGCACAGA AGCCTCTTGA GTCCCGGCGA TCCAGCGGCC   650
 CAGACTTCTG ACATCCTGGA GAGGCTGGCC CACGATGGAA ACTGGGAGGC   700
 CCTGAGAGTT GAGGGACGTG GAGCTCCTTG TGGAGAGAGT GGGTGGGCTG   750
 AGAAGACACC ACCAAGGGGC CTGCGCCCTC GCCCTCGCCC TCGCCCTCCT   800
 CTCGCCGGGC TCTGCAGGCG GGGAGGTGGA GAGCTGGGA  GTGGCGTGCA   850
 AGGCAGGCGT CCCGGTGACG CAGGGCCTGG TGCATTTCTC CAGCTTGGTC   900
 TTCTGACCTG GCCCTTGTCT GACGTCCCCC TAAGGCGAAG AAAAGCAGGT   950
 TCCTGCCGGG GTAACCAGAG GGCTCGCGGA GCAGAAGCGC GCCAGGCACG  1000
 TTACTGTAAG CTGCGTGCGC AGAAACCAAC GCGCTGGGTG GCGGGCGACG  1050
 CGAGCCGCCG CGGACACCGG CCCGGACAGC TGGACCGTGG CGCACTAGCC  1100
 GCTTCCTAAA TGATTGCCCG GAGTGACTCG CCGAGACCCC GTGTGTACAC  1150
 AAGTCGGACG AGGGCGGGC  GCACAGCGGC CAGGAAGTCG GGCCCAGCG   1200
 CACCCCTCAG CGGACCATCC CGCTCCGTGG GGCCGGACAG GACCCCGGA   1250
 CCACGCGGA  GCGATGCAAG GTCCGTTCCC GCTGCGCGCA CTTGCGGCCC  1300
 GCAGCCCCGG CCCTCGGAGC TGCCACGGCT CCCAGCGTGT TCTGCGCCGG  1350
 TGCGGCCGCG GCGACTACGA CTCCCAGGGT GCTCTGCGCC GGCGCGCCG   1400
 CGGCGACTAC GACTCCCAGG GTGCCCTGCG CCCGGTCAGC CTCTCCAGGC  1450
 CCGGCCTCAG GTCGGCCGCG GACTACAAAT GGACGAGAGA GGCGGCCGTC  1500
 CATTAGTTAG CCGCTCCGGA GCAACGCAGC CGTTGTCCTT GAGGCCGACG  1550
 GGCCTGACGC GGGGCGGTTG AACGCGCTGG TGAGGCGGTC ACCGGGCTA   1600
 CGGCGGCGG  CAGGGGCAG  TGGCGGCCGT TGTCTAGGGC CCGAGGTGG   1650
 GGCCGCGCGC CTGGGCGCT  ACGAACCGG  CAGGCCCACG CTTGGCTGCG  1700
 GCGGGTGCGG CGCTGAGGCC ATGGGCGACC GCGGCAGCTC CGGCGGCGG   1750
 AGGACAGGGT CGCGGCCCTC GAGCCACGGC GGCGGCGGC  CTGCCGCGGC  1800
```

FIG. 1A

```
         10         20         30         40         50
1234567890 1234567890 1234567890 1234567890 1234567890
GGAAGAGGAG GTGCGGGACG CCGCTGCGGG CCCCGACGTG GGAGCCGCGG    1850
GGGACGCGCC AGCCCCGGCC CCCAACAAGG ACGGAGACGC CGGCGTGCGC    1900
AGCGGCCACT GGGAGCTGAG GTAGCGGACC GCCTGACCCC CTAACCTCTG    1950
ACCCAAGGGC CCCGCGACTT TCCGCGGTTG GCCGAAGCGC GAGCTCCGAG    2000
TCCGAGAACA TGGCCCCTGG GCTAAGCCGG GATCGGTGTG CCCTATGGGC    2050
CCTGTGGGGA AACTGAGGCT TGGGGAGAGT CACCTGACAA GGTCACTGGG    2100
TAGGGGCTCT GGACTGCCTT GCCAGGCAGA GGGGAGCCGG CAGGTGTCCG    2150
CATCCAGATC CTCTTGGTCT GTGC                                2174
```

FIG. 1B

GG allele →
CC allele →

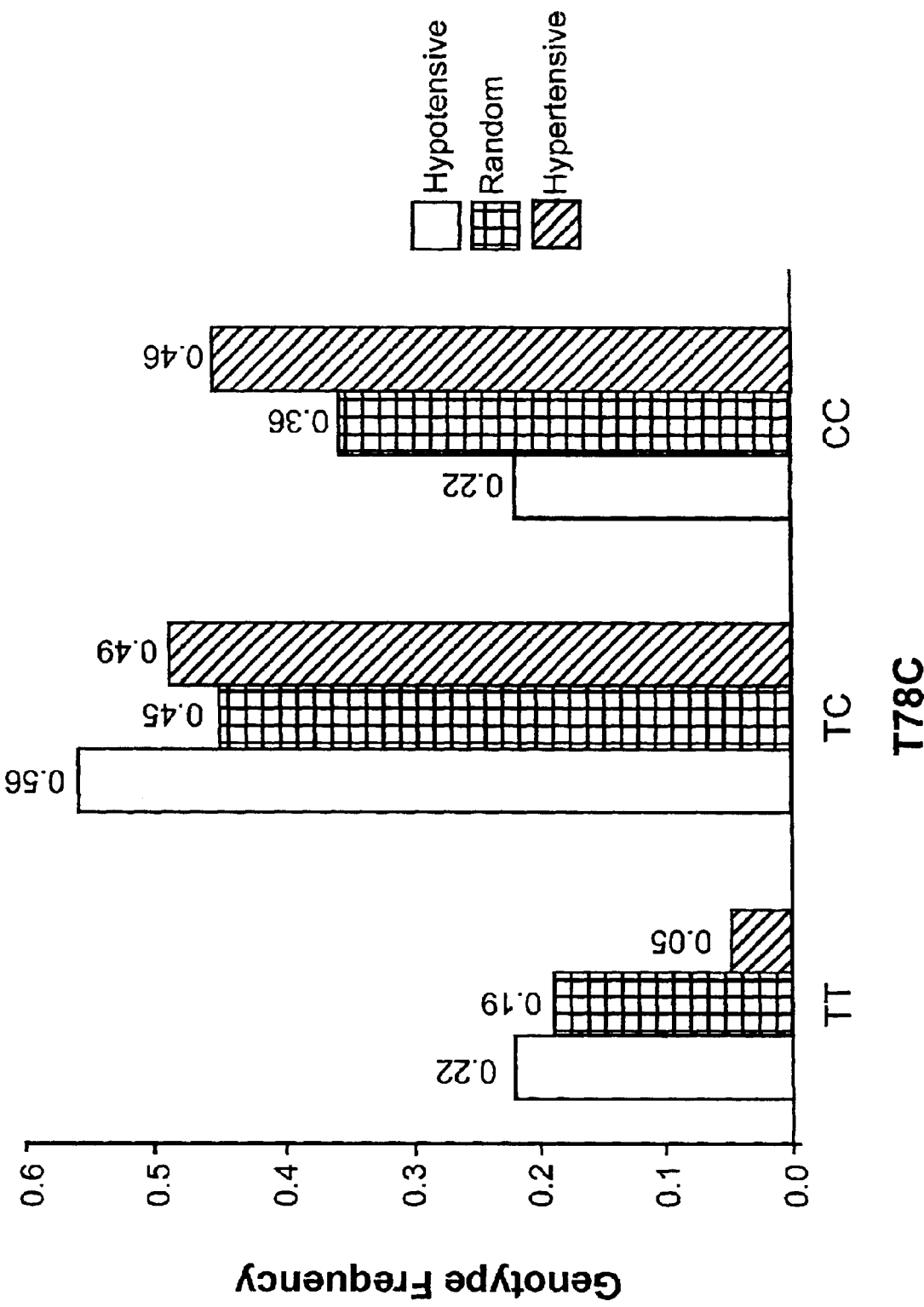

POLYMORPHISMS IN A DIACYLGLYCEROL ACYLTRANSFERASE GENE, AND METHODS OF USE THEREOF

CROSS REFERENCE TO RELATED APPLICATIONS

This application is a continuation of U.S. patent application Ser. No. 09/613,444, filed Jul. 11, 2000, now U.S. Pat. No. 6,444,427 which application is incorporated herein by reference in its entirety.

FIELD OF THE INVENTION

This invention is in the field of genetic polymorphisms, particularly polymorphisms in a diacylglycerol acyltransferase gene.

BACKGROUND OF THE INVENTION

Triacylglycerols are quantitatively the most important storage form of energy in eukaryotes. Triglyceride synthesis is thought to occur primarily through acyl CoA:diacylglycerol transferase (DGAT), a microsomal enzyme. Diacylglycerol acyl-transferase (DGAT; acyl CoA:diacylglycerol acyltransferase; EC 2.3.1.20) is a ubiquitous enzyme that catalyzes the synthesis of triglycerides by adding a fatty acid to diacylglycerol. DGAT plays a fundamental role in the metabolism of cellular diacylglycerol, and is important in higher eukaryotes for physiologic processes involving triacylglycerol metabolism, such as intestinal fat absorption, lipoprotein assembly, adipose tissue formation, and lactation. Cases et al. (1998) *Proc. Natl. Acad. Sci. USA* 95:13018–13023.

Abnormal fat storage causes, or is related to, a variety of debilitating, and often lethal, conditions As one example, obesity, generally defined as a condition of being 20% or more over ideal body weight, affects an estimated 34 million Americans, and is a major cause of death in the Unites States. Morbid obesity, a much more severe form of obesity in which a person is 100 or more pounds overweight, affects an estimated four million Americans. One important consequence of obesity is maturity-onset (Type II) diabetes. Obesity is also linked to, or increases the risk of, hypertension, atherosclerosis, and myocardial infarction, as well as other serious disorders. Hypertension alone affects approximately 50 million Americans, and increases the risk of heart disease and stroke, which are leading causes of death among Americans. The profound negative health and social consequences of obesity have provided the impetus for development of a large number of drugs for control of this condition. Bray and Greenway (1999) *Endocrinol. Rev.* 20:805–875. While several genes and mutations have been identified that contribute to obesity and other common metabolic disorders, they represent a small fraction of the genetic causes of obesity. Chagnon et al. (2000) *Obesity Res.* 8:89–117; and Barsh et al. (2000) *Nature* 404:644–651.

Despite advances in detecting mutations and genes associated with obesity, obesity continues to exert adverse effects on human health. Thus, there is a need in the art for identification of additional information regarding genes and gene mutations associated with obesity. Such information is crucial for identifying individuals who have a propensity toward becoming obese, and for identifying new therapeutic targets for control of obesity. The present invention addresses this need by providing polymorphisms associated with conditions associated with DGAT activity, including, e.g., obesity.

SUMMARY OF THE INVENTION

The present invention provides an isolated polynucleotide comprising a polymorphic nucleotide sequence from a diacylglycerol acyltransferase (DGAT) gene. The polymorphism may be in a coding or non-coding portion of the gene. In some embodiments, polymorphisms are associated with a condition associated with DGAT activity. In some of these embodiments, the polymorphism is associated with a condition relating to abnormal fat storage. In particular embodiments, polymorphisms are associated with obesity. Isolated polynucleotides comprising one or more polymorphisms in a DGAT gene that are associated with a condition associated with DGAT activity are useful in diagnostic assays.

Accordingly, the invention further provides diagnostic assays for detecting the presence in a nucleic acid sample of a polymorphism in a DGAT gene that is associated with a condition associated with DGAT activity. Diagnostic assays are useful in predicting an individual's likelihood of developing a condition associated with DGAT activity. Thus, the invention further provides methods of detecting a propensity in an individual of developing a condition associated with DGAT activity. The invention further provides methods for genetically diagnosing in an individual a condition associated with DGAT activity. These methods generally involve detecting in a nucleic acid sample derived from an individual a DGAT polymorphism associated with a condition associated with DGAT activity. In some embodiments, diagnostic assays are conducted using a microarray comprising a DGAT polymorphic nucleic acid molecule.

Detection of DGAT polymorphisms associated with a condition associated with DGAT activity allows selection of a treatment plan that is most likely to be effective in treating the condition. Thus, the invention further provides methods for treating an individual clinically diagnosed with a condition associated with DGAT activity, generally comprising detecting a DGAT polymorphism associated with a condition associated with DGAT activity, and selecting a treatment plan that is most effective for individuals clinically diagnosed as having a condition associated with DGAT activity. Detection of DGAT polymorphisms associated with a condition associated with DGAT activity also allows one to predict a patient's likelihood to respond to a specific drug treatment. Thus, the invention further provides methods of predicting a patient's likelihood to respond to a specific drug treatment for a condition associated with DGAT activity.

The invention further provides an array of nucleic acid molecules immobilized on a solid surface, where at least one of the nucleic acid molecules comprises a DGAT polymorphic nucleic acid molecule. The nucleic acid arrays of the invention allow rapid detection of hybridizing nucleic acid-molecules, in a nucleic acid sample from an individual, of a DGAT polymorphism associated with a condition relating to abnormal fat storage.

The invention further provides isolated polymorphic DGAT polypeptides, as well as antibodies specific for polymorphic DGAT polypeptides. The specific antibodies are useful in assays for detecting the presence of a polymorphic DGAT polypeptide in a biological sample. In carrying out these detection assays, antibodies bound to a solid support may be used. Thus, the invention further provides assay devices comprising antibodies specific for polymorphic DGAT polypeptides, where the antibodies are attached to a solid support.

These and other aspects of the invention will become apparent to those persons skilled in the art upon reading the details of the invention as more fully described below.

BRIEF DESCRIPTION OF THE DRAWINGS

FIG. 1 provides a nucleotide sequence of a 5' region of a human DGAT gene SEQ ID NO:1.

FIG. 6 is a graph depicting the distribution and frequency of the T78C polymorphism in hypotensive, random, and hypertensive Turkish women.

DETAILED DESCRIPTION OF THE INVENTION

Figure 2:
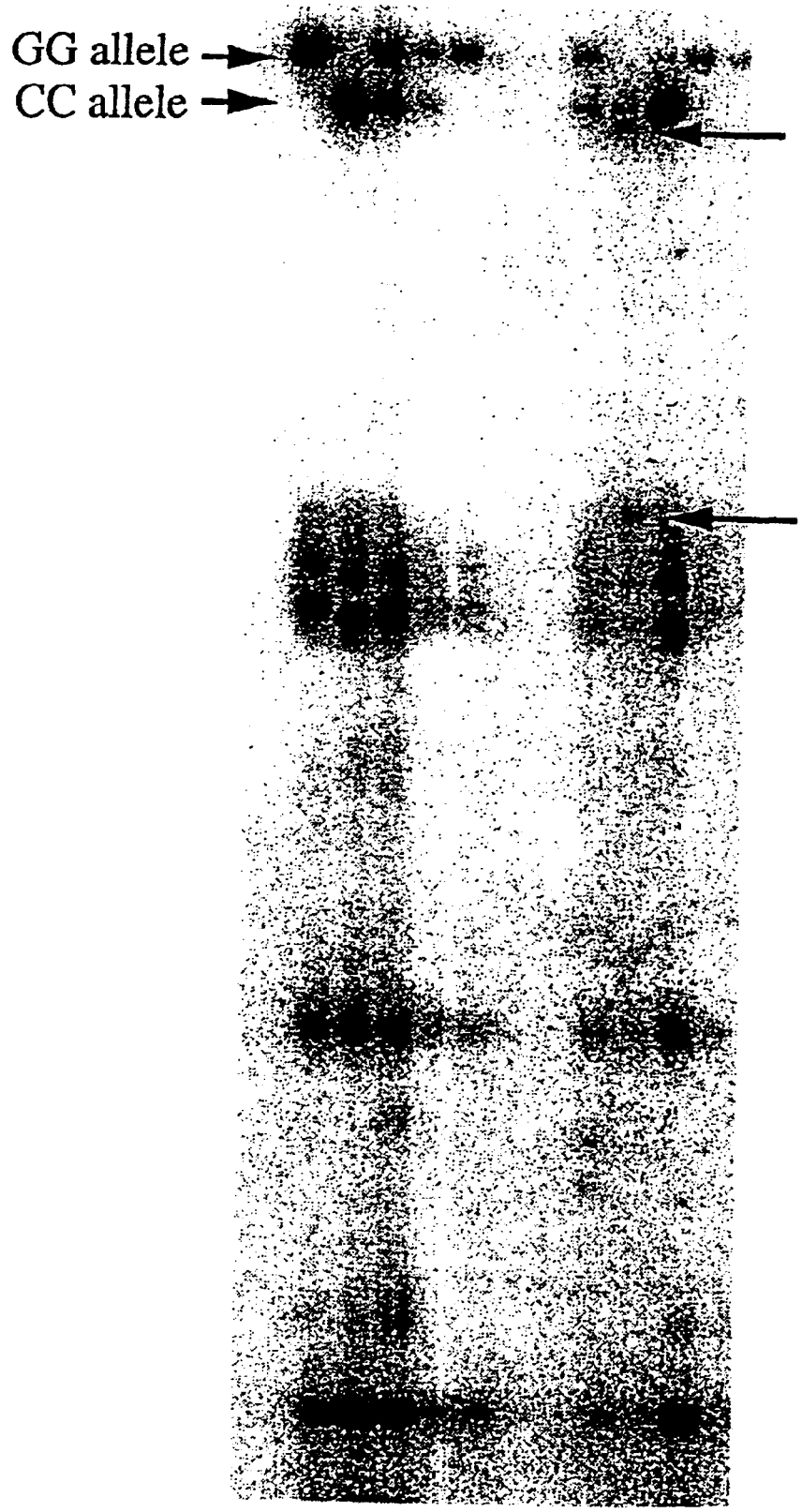
FIG. 2 is an autoradiograph depicting single-stranded conformation polymorphism analysis of a DGAT promoter.

The present invention provides polymorphisms in a diacylglycerol acyltransferase (DGAT) gene which are associated with a condition associated with DGAT activity, and methods of using nucleic acid molecules comprising the polymorphisms. The invention is based on the finding that particular polymorphisms in the human DGAT gene are associated in a statistically significant manner with the occurrence of conditions such as abnormal serum cholesterol levels, hypertension, and obesity. These observations have allowed development of diagnostic assays to detect the presence of polymorphisms in an individual, which polymorphisms are associated with a condition associated with DGAT activity, and hence to predict the likelihood that an individual will develop a condition associated with DGAT activity.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a polymorphism includes a plurality of such polymorphisms, reference to "a nucleic acid molecule" includes a plurality of such nucleic acid molecules, and reference to "the method" includes reference to one or more methods, method steps, and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

As used herein, the term "DGAT gene" is intended to generically refer to both the wild-type and variant forms of the sequence, unless specifically denoted otherwise. As it is commonly used in the art, the term "gene" is intended to refer to the genomic region encompassing 5' untranslated region(s) (UTR), exons, introns, and 3' UTR. Individual segments may be specifically referred to, e.g. exon 2, intron 5, etc. Combinations of such segments that provide for a complete DGAT protein may be referred to generically as a protein coding sequence. The nucleotide sequences of DGAT mRNA are publicly available through GenBank: Accession No. NM-012079 (human DGAT mRNA) and Accession No. NM-010046 (mouse DGAT mRNA).

The term "polymorphism", as used herein, refers to a difference in the nucleotide or amino acid sequence of a given region as compared to a nucleotide or amino acid sequence in a homologous-region of another individual, in particular, a difference in the nucleotide of amino acid sequence of a given region which differs between individuals of the same species. A polymorphism is generally defined in relation to a reference sequence. Polymorphisms include single nucleotide differences, differences in sequence of more than one nucleotide, and single or multiple nucleotide insertions, inversions and deletions; as well as single amino acid differences, differences in sequence of more than one amino acid, and single or multiple amino acid insertions, inversions, and deletions.

As used herein, the term "polymorphic DGAT nucleic acid molecule" refers to a polynucleotide derived from a DGAT gene, which polynucleotide comprises one or more polymorphisms when compared to a reference DGAT polynucleotide sequence. A polymorphism in a polymorphic DGAT nucleic acid molecule may be one that is associated with a condition relating to DGAT activity.

The terms "polynucleotide" and "nucleic acid molecule" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art. Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

In the broadest sense, as used herein, the terms "a condition associated with DGAT activity," and "a disease condition associated with DGAT activity," refer to a condition or disease which results, directly or indirectly, from altered DGAT activity. "Altered DGAT activity," as used herein, includes one or more of the following: (1) DGAT enzymatic activity that is higher or lower than normal DGAT enzymatic activity; (2) a level of DGAT mRNA in a cell that is higher or lower than the normal level of DGAT mRNA for that cell type; and (3) a level of DGAT polypeptide that is higher or lower than the normal level of DGAT polypeptide. A condition associated with DGAT activity is also a condition or disease which is symptomatic of altered DGAT activity. "Normal DGAT enzymatic activity," "normal DGAT mRNA levels," and "normal DGAT polypeptide levels" refer to DGAT activity that is in the normal range for an individual of a given species, and which is not associated with, or give rise to, a disease condition. A condition associated with DGAT activity-includes, but is not limited to, elevated serum levels of triglyceride (e.g., serum levels of triglycerides in excess of about 500 mg %); elevated serum levels of cholesterol; lower than normal serum levels of HDL; and lipid disorders. A representative type of a condition associated with DGAT activity is a condition related to abnormal fat storage.

As used herein, the terms "a condition related to abnormal fat storage," and "a condition related to abnormal fat metabolism," are used interchangeably herein and refer to a condition (also referred to herein as a "disease" or a "disorder"), which is a direct or indirect result of, abnormal fat storage. It is also a condition that is symptomatic of abnormal fat storage. It is also a condition that occurs as a consequence of abnormal fat storage. Conditions associated with abnormal fat storage include, but are not limited to, obesity; severe leanness; hypertension; atherosclerosis; Type II diabetes; osteoarthritis; breast cancer; uterine cancer; colon cancer; and coronary artery disease.

The term "obesity," as used herein, refers to a condition associated with excessive caloric intake relative to energy output such that excessive body fat accumulates. A standard measurement of obesity is body-mass index (BMI), which is defined as weight in kilograms divided by the square of the height in meters. A BMI of about 22 to about 25 is considered the normal range for humans. A BMI of ≦19 is considered underweight ("severe leanness"). A BMI of 27 to 29.9 is considered overweight. The World Health Organization criterion for obesity is a BMI of 30 or greater. Obese individuals are further categorized into obesity classes: class I, BMI=30.0–34.9; class II, BMI=35.0 to 39.9; and class III, BMI=≧40. Thus, "an obese individual" is one having a BMI of 30 or greater, and "a non-obese individual is one having a BMI of 29.9 or less.

The term "hypertension," as used herein, refers to a condition identified by a systolic blood pressure of about 140 mm Hg or higher, a diastolic blood pressure of about 90 mm Hg or greater, or both.

The terms "a propensity to develop a condition associated with DGAT activity," as used herein, refers to a statistically significant increase in the probability of developing measurable characteristics of a condition associated with DGAT activity in an individual having a particular genetic lesion(s) or polymorphism(s) compared with the probability in an individual lacking the genetic lesion or polymorphism.

A "substantially isolated" or "isolated" polynucleotide is one that is substantially free of the sequences with which it is associated in nature. By substantially free is meant at least 50%, preferably at least 70%, more preferably at least 80%, and even more preferably at least 90% free of the materials with which it is associated in nature. As used herein, an "isolated" polynucleotide also refers to recombinant polynucleotides, which, by virtue of origin or manipulation: (1) are not associated with all or a portion of a polynucleotide with which it is associated in nature, (2) are linked to a polynucleotide other than that to which it is linked in nature, or (3) does not occur in nature.

Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. Examples of stringent conditions are hybridization and washing at 50° C. or higher and in 0.1×SSC (9 mM NaCl/0.9 mM sodium citrate).

"$T_m$" is the temperature in degrees Celsius at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as:

$$T_m = 81.5 + 16.6 \log [X^+] + 0.41(\%G/C) - 0.61(\%F) - 600/L$$

where [X⁺] is the cation concentration (usually sodium ion, Na⁺) in mol/L; (%G/C) is the number of G and C residues as a percentage of total residues in the duplex; (%F) is the percent formamide in solution (wt/vol); and L is the number of nucleotides in each strand of the duplex.

Stringent conditions for both DNA/DNA and DNA/RNA hybridization are as described by Sambrook et al. *Molecular Cloning, A Laboratory Manual,* 2nd Ed., Cold Spring Harbor Laboratory Press, Cold Spring Harbor, N.Y., 1989, herein incorporated by reference. For example, see page 7.52 of Sambrook et al.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells tranfected or infected in vivo or in vitro with a recombinant vector or a polynucleotide of the invention. A host cell which comprises a recombinant vector of the invention is a "recombinant host cell".

The term "binds specifically," in the context of antibody binding, refers to high avidity and/or high affinity binding of an antibody to a specific polypeptide i.e., epitope of a polymorphic DGAT polypeptide. Antibody binding to an epitope on a specific polymorphic DGAT polypeptide (also referred to herein as "a polymorphic DGAT epitope") is preferably stronger than binding of the same antibody to any other epitope, particularly those which may be present in molecules in association with, or in the same sample, as the specific polypeptide of interest, e.g., binds more strongly to a specific DGAT polymorphic epitope than to a different DGAT epitope so that by adjusting binding conditions the antibody binds almost exclusively to the specific DGAT polymorphic epitope and not to any other DGAT epitope, and not to any other DGAT polypeptide which does not comprise the polymorphic epitope. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls. In general, antibodies of the invention which bind to a specific polymorphic DGAT polypeptide with a binding affinity of $10^7$ mole/l or more, preferably $10^8$ mole/liters or more are said to bind specifically to the specific DGAT polymorphic polypeptide. In general, an antibody with a binding affinity of $10^6$ mole/liters or less is not useful in that it will not bind an antigen at a detectable level using conventional methodology currently used.

The terms "detectably labeled antibody," "detectably labeled anti-polymorphic DGAT polypeptide," "detectably labeled anti-DGAT polymorphic epitope," or "detectably labeled anti-DGAT polymorphic polypeptide fragment" refer to an antibody (or antibody fragment which retains binding specificity for a polymorphic DGAT polypeptide or epitope), having an attached detectable label. The detectable label is normally attached by-chemical conjugation, but where the label is a polypeptide, it could alternatively be attached by genetic engineering techniques. Methods for production of detectably labeled proteins are well known in the art. Detectable labels may be selected from a variety of such labels known in the art, including, but not limited to, radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/ diaminobenzidine, avidin/streptavidin, luciferase/ luciferin)), methods for labeling antibodies, and methods for using labeled antibodies are well known in the art (see, for example, Harlow and Lane, eds. (*Antibodies: A Laboratory Manual* (1988) Cold Spring Harbor Laboratory Press, Cold Spring Harbor, N.Y.)).

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," and "patient," used interchangeably herein, refer to a mammal, including, but not limited to, murines, simians, humans, mammalian farm animals, mammalian sport animals, and mammalian pets.

Isolated Polymorphic DGAT Nucleic Acid Molecules

The present invention provides isolated polynucleotides comprising one or more DGAT polymorphic nucleic acid molecules. In some embodiments, the polymorphism is one that is associated with a condition associated with DGAT activity. The isolated polynucleotides are useful in a variety of diagnostic methods. Isolated polymorphic DGAT nucleic acid molecules of the invention can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

DGAT genes have been disclosed. Cases et al. (1998) *Proc. Natl. Acad. Sci. USA* 95: 13018–13023. The source of DGAT gene suitable for use in the present invention can be any mammalian DGAT gene. In general, for diagnostic assays, the animal source of the DGAT gene will be the same species as the animal whose nucleic acid is being tested.

An isolated polymorphic DGAT nucleic acid molecule comprises one or more DGAT polymorphisms. In some embodiments, a polymorphic DGAT sequence comprises one or more of the following polymorphisms: (1) a GG→CC variation at about nucleotides −656 and −657 relative to the DGAT gene transcription start site; (2) a T→C variation at about nucleotide 78 relative to the DGAT gene transcription start site; (3) a G→A variation at about nucleotide 205 relative to the DGAT gene transcription start site; (4) an A→T variation at about −792 relative to the DGAT gene transcription start site; (5) a G→T variation at about −402 relative to the DGAT gene transcription start site; a T→C at about 137 relative to the DGAT gene transcription start site. The exact position of the aforementioned variants may vary from individual to individual or from species to species, e.g., by from 1 to about 10 base pairs.

For some uses, e.g., in screening assays, DGAT polymorphic nucleic acid molecules will be of at least about 15 nucleotides (nt), at least about 18 nt, at least about 20 nt, or at least about 25 nt in length, and often at least about 50 nt. Such small DNA fragments are useful as primers for polymerase chain reaction (PCR), hybridization screening, etc. Larger polynucleotide fragments, e.g., at least about 50 nt, at least about 100 nt, at least about 200 nt, at least about 300 nt, at least about 500 nt, at least about 1000 nt, at least about 1500 nt, up to the entire coding region, or up to the entire coding region plus up to about 1000 nt 5' and/or up to about 1000 nt 3' flanking sequences from a DGAT gene, are useful for production of the encoded polypeptide, promoter motifs, etc. For use in amplification reactions, such as PCR, a pair of primers will be used. The exact composition of primer sequences is not critical to the invention, but for most applications the primers will hybridize to the subject sequence under stringent conditions, as known in the art.

When used as a probe, an isolated polymorphic DGAT nucleic acid molecule may comprise non-DGAT nucleotide sequences, as long as the additional non-DGAT nucleotide sequences do not interfere with the detection assay. A probe may comprise an isolated polymorphic DGAT sequence, and any number of non-DGAT nucleotide sequences, e.g., from about 1 bp to about 1 kb or more.

For screening purposes, hybridization probes of the polymorphic sequences may be used where both forms are present, either in separate reactions, spatially separated on a solid phase matrix, or labeled such that they can be distinguished from each other. Assays (described below) may utilize nucleic acids that hybridize to one or more of the described polymorphisms.

Isolated polymorphic DGAT nucleic acid molecules of the invention may be coupled (e.g., chemically conjugated), directly or indirectly (e.g., through a linker molecule) to a solid substrate. Solid substrates may be any known in the art including, but not limited to, beads, e.g., polystyrene beads; chips, e.g., glass, $SiO_2$, and the like; plastic surfaces, e.g., polystyrene, polycarbonate plastic multi-well plates; and the like.

Isolated polymorphic DGAT nucleic acid molecules can be obtained by chemical or biochemical synthesis, by recombinant DNA techniques, or by isolating the nucleic acids from a biological source, or a combination of any of the foregoing. For example, the nucleic acid may be synthesized using solid phase synthesis techniques, as are known in the art. Oligonucleotide synthesis is also described in Edge et al. (1981) *Nature* 292:756; Duckworth et al. (1981) *Nucleic Acids Res.* 9:1691 and Beaucage and Caruthers (1981) *Tet. Letters* 22:1859. Following preparation of the nucleic acid, the nucleic acid is then ligated to other members of the expression system to produce an expression cassette or system comprising a nucleic acid encoding the subject product in operational combination with transcriptional initiation and termination regions, which provide for expression of the nucleic acid into the subject polypeptide products under suitable conditions.

Additional DGAT gene polymorphisms may be identified using any of a variety of methods known in the art, including, but not limited to SSCP, denaturing HPLC, and sequencing. Example 1 provides a description of how DGAT polymorphisms were identified using single strand conformation polymorphism (SSCP) analysis and denaturing HPLC analysis. SSCP may be used to identify additional DGAT gene polymorphisms. In general, PCR primers and restriction enzymes are chosen so as to generate products in a size range of from about 25 bp to about 500 bp, or from about 100 bp to about 250 bp, or any intermediate or overlapping range therein.

Polymorphic DGAT Polypeptides

The present invention provides isolated polymorphic DGAT polypeptides. Isolated polymorphic DGAT polypeptides are useful in assays to screen for agents that modify an enzymatic activity of a DGAT polypeptide.

The term "polymorphic DGAT polypeptide" encompasses an amino acid sequence encoded by an open reading frame (ORF) of a known DGAT polynucleotide, including the full-length native polypeptide and fragments thereof, particularly biologically active fragments and/or fragments corresponding to functional domains, e.g. a region or domain having enzymatic activity, etc.; antigenic fragments thereof, and including fusions of the subject polypeptides to other proteins or parts thereof. The amino acid sequences of DGAT polypeptides have been disclosed. See, e.g., Cases et al. (1998) *Proc. Natl. Acad. Sci. USA* 95:13018–13023. A polymorphism in a DGAT polypeptide is generally defined relative to a reference sequence.

As used herein, "polymorphic DGAT polypeptide" refers to an amino acid sequence of a recombinant or non-recombinant polypeptide having an amino acid sequence of i) a native polymorphic DGAT polypeptide, ii) a fragment of a polymorphic DGAT polypeptide, iii) polypeptide analogs of a polymorphic DGAT polypeptide, iv) variants of a polymorphic DGAT polypeptide; v) an immunologically active fragment of a polymorphic DGAT polypeptide; and vi) fusion proteins comprising a polymorphic DGAT polypeptide. Polymorphic DGAT polypeptides of the invention can be obtained from a biological sample, or from any source whether natural, synthetic, semi-synthetic or recombinant.

The term "polymorphic DGAT polypeptide" encompasses a polypeptide comprising from at least about 5 amino acids, at least about 10 amino acids, at least about 15 amino acids, at least about 25 amino acids, at least about 50 amino acids, at least about 75 amino acids, at least about 100 amino acids, at least about 200 amino acids, at least about 300 amino acids, at least about 400 amino acids, or up to the entire polypeptide of a polymorphic DGAT polypeptide. In some embodiments, a polymorphic DGAT polypeptide exhibits enzymatic activity, e.g., the polypeptide catalyzes the addition of a fatty acid moiety to diacyl glycerol. Assays for DGAT enzymatic activity are known in the art and can be used to determine whether a polymorphic DGAT polypeptide exhibits enzymatic activity and, if desired, to quantitate DGAT enzymatic activity. In general, a detectably-labeled fatty acyl CoA molecule and diacylglycerol (DAG) are used as substrates, and incorporation of labeled fatty acid into the triglyceride product is measured. DGAT enzymatic assays are described in various publications, e.g., Cases et al. (1998) *Proc. Natl. Acad. Sci. USA* 95:13018–13023.

Polymorphic DGAT polypeptides of the invention may be part of a fusion protein. Suitable fusion partners (e.g., a non-DGAT polypeptide, or "heterologous polypeptide") include, but are not limited to, a heterologous polypeptide that provides for immunological recognition, e.g., an epitope tag; a heterologous polypeptide that provides for a detectable signal, e.g., a green fluorescent protein (GFP), β-galactosidase, and the like; a heterologous polypeptide that provides for a catalytic function; and a heterologous polypeptide that facilitates entry into a cell. The fusion partner can be coupled in-frame to the N-terminus, the C-terminus, or both of the polymorphic DGAT polypeptide, using standard methods for synthesis of polypeptides, or using recombinant methods.

Polymorphic DGAT polypeptides of the invention can be obtained by any known method, or a combination of such methods, including isolation from natural sources; production by chemical synthesis; and production by standard recombinant techniques.

Polymorphic DGAT polypeptides can be isolated from a biological source, using affinity chromatography, e.g., using antibodies specific for a DGAT polypeptide are immobilized on a solid support. The polypeptides may be expressed in prokaryotes or eukaryotes in accordance with conventional ways, depending upon the purpose for expression. For large scale production of the protein, a unicellular organism, such as E. coli, B. subtilis, S. cerevisiae, insect cells in combination with baculovirus vectors, or cells of a higher organism such as vertebrates, particularly mammals, e.g. COS 7 cells, CHO cells, HEK293 cells, and the like, may be used as the expression host cells. In some situations, it is desirable to express the gene in eukaryotic cells, where the protein will benefit from native folding and post-translational modifications. The polypeptide can then be isolated from cell culture supernatant or from cell lysates using affinity chromatography methods or anion exchange/size exclusion chromatography methods, as described above.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique.

Vectors and Host Cells Comprising the Polynucleotides of the Invention

The invention further provides recombinant vectors and host cells comprising polynucleotides of the invention. In general, recombinant vectors and host cells of the invention are isolated; however, a host cell comprising a polynucleotide of the invention may be part of a genetically modified animal.

Recombinant vectors. The present invention further provides recombinant vectors ("constructs") comprising a polynucleotide of the invention. Recombinant vectors include vectors used for propagation of a polynucleotide of the invention, and expression vectors. Vectors useful for introduction of the polynucleotide include plasmids and viral vectors, e.g. retroviral-based vectors, adenovirus vectors, etc. that are maintained transiently or stably in mammalian cells. A wide variety of vectors can be employed for transfection and/or integration of the gene into the genome of the cells. Alternatively, micro-injection may be employed, fusion, or the like for introduction of genes into a suitable host cell.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, at least about 25 amino acids, at least about 45 amino acids, and up to the complete open reading frame of the gene. After introduction of the DNA, the cells containing the construct may be selected by means of a selectable marker, the cells expanded and then used for expression.

The expression cassettes may be introduced into a variety of vectors, e.g. plasmid, BAC, YAC, bacteriophage such as lambda, P1, M13, etc., animal or plant viruses, and the like, where the vectors are normally characterized by the ability to provide selection of cells comprising the expression vectors. The vectors may provide for extrachromosomal maintenance, particularly as plasmids or viruses, or for integration into the host chromosome. Where extrachromosomal maintenance is desired, an origin sequence is provided for the replication of the plasmid, which may be low- or high copy-number. A wide variety of markers are available for selection, particularly those which protect against toxins, more particularly against antibiotics. The particular marker that is chosen is selected in accordance with the nature of the host, where in some cases, complementation may be employed with auxotrophic hosts. Introduction of the DNA construct may use any convenient method, e.g. conjugation, bacterial transformation, calcium-precipitated DNA, electroporation, fusion, transfection, infection with viral vectors, biolistics, etc.

Genetically Modified Cells. The present invention further provides host cells, which may be isolated host cells, comprising polymorphic DGAT nucleic acid molecules of the invention. Suitable host cells include prokaryotes such as E. coli, B. subtilis, eukaryotes, including insect cells in combination with baculovirus vectors, yeast cells, such as Saccharomyces cerevisiae, or cells of a higher organism such as vertebrates, including amphibians (e.g., Xenopus laevis oocytes), and mammals, particularly humans, e.g. COS cells, CHO cells, HEK293 cells, and the like, may be used as the host cells. Host cells can be used for the purposes of propagating a polymorphic DGAT nucleic acid molecule, for production of a polymorphic DGAT polypeptide, or in cell-based methods for identifying agents which modulate a level of DGAT mRNA and/or protein and/or enzyme activity in a cell.

Primary or cloned cells and cell lines may be modified by the introduction of vectors comprising a DGAT gene polymorphism(s). The isolated polymorphic DGAT nucleic acid molecule may comprise one or more variant sequences, e.g., a haplotype of commonly occurring combinations. In one embodiment of the invention, a panel of two or more genetically modified cell lines, each cell line comprising a DGAT polymorphism, are provided for substrate and/or expression assays. The panel may further comprise cells genetically modified with other genetic sequences, including polymorphisms, particularly other sequences of interest for pharmacogenetic screening, e.g. other genes/gene mutations associated with obesity, a number of which are known in the art.

Transgenic animals. The subject nucleic acids can be used to generate genetically modified non-human animals or site specific gene modifications in cell lines. The term "transgenic" is intended to encompass genetically modified animals having a deletion or other knock-out of DGAT gene activity, having an exogenous DGAT gene that is stably transmitted in the host cells, or having an exogenous DGAT promoter operably linked to a reporter gene. Transgenic animals may be made through homologous recombination, where the DGAT locus is altered. Alternatively, a nucleic acid construct is randomly integrated into the genome. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

DNA constructs for homologous recombination will comprise at least a portion of a polymorphic DGAT nucleic acid molecule, and will include regions of homology to the target locus. Conveniently, markers for positive and negative selection are included. Methods for generating cells having targeted gene modifications through homologous recombination are known in the-art. For various techniques for transfecting mammalian cells, see Known et al. (1990) *Methods in Enzymology* 185:527–537.

For embryonic stem (ES) cells, an ES cell line may be employed, or ES cells may be obtained freshly from a host, e.g. mouse, rat, guinea pig, etc. Such cells are grown on an appropriate fibroblast-feeder layer or grown in the presence of leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination. Those colonies that show homologous recombination may then be used for embryo manipulation and blastocyst injection. Blastocysts are obtained from. 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected. The chimeric animals are screened for the presence of the DGAT gene and males and females having the modification are mated to produce homozygous progeny. The transgenic animals may be any non-human mammal, such as laboratory animals, domestic animals, etc. The transgenic animals may be used to determine the effect of a candidate drug on triglyceride synthesis in an in vivo environment.

Preparation of Polymorphic DGAT Polypeptides

In addition to the plurality of uses described in greater detail in following sections, the subject nucleic acid compositions find use in the preparation of all or a portion of the polymorphic DGAT polypeptides, as described above. The subject polynucleotides (including cDNA or the full-length gene) is used to express a partial or complete gene product. Constructs comprising the subject polynucleotides can be generated synthetically. Alternatively, single-step assembly of a gene and entire plasmid from large numbers of oligodeoxyribonucleotides is described by, e.g., Stemmer et al., *Gene (Amsterdam)* (1995) 164(1):49–53. In this method, assembly PCR (the synthesis of long DNA sequences from large numbers of oligodeoxyribonucleotides (oligos)) is described. The method is derived from DNA shuffling (Stemmer, *Nature* (1994) 370:389–391), and does not rely on DNA ligase, but instead relies on DNA polymerase to build increasingly longer DNA fragments during the assembly process. Appropriate polynucleotide constructs are purified using standard recombinant DNA techniques as described in, for example, Sambrook et al., *Molecular Cloning: A Laboratory Manual,* 2nd Ed., (1989) Cold Spring Harbor Press, Cold Spring Harbor, N.Y., and under current regulations described in United States Dept. of HHS, National Institute of Health (NIH) Guidelines for Recombinant DNA Research.

Polynucleotide molecules comprising a polynucleotide sequence provided herein are propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. The gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, an polymorphic DGAT polypeptide-encoding polynucleotide is linked to a regulatory sequence as appropriate to obtain the desired expression properties. These-can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the DGAT gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

Polymorphic DGAT polypeptides may be expressed in prokaryotes or eukaryotes in accordance with conventional ways, depending upon the purpose for expression. For large scale production of the protein, a unicellular organism, such as E. coli, B. subtilis, S. cerevisiae, insect cells in combination with baculovirus vectors, or cells of a higher organism such as vertebrates, particularly mammals, e.g. COS 7 cells, HEK 293, CHO, Xenopus Oocytes, etc., may be used as the expression host cells. In some situations, it is desirable to express a polymorphic DGAT nucleic acid molecule in eukaryotic cells, where the polymorphic DGAT protein will benefit from native folding and post-translational modifications. Small peptides can also be synthesized in the laboratory. Polypeptides that are subsets of the complete DGAT sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci.* (*USA*) (1983) 80:21–25; and Siebenlist et al., *Cell* (1980) 20:269.

Yeast. Expression systems in yeast include those described in Hinnen et al., *Proc. Natl. Acad. Sci.* (*USA*) (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985)25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154:737; Van den Berg et al., *Bio/Technology* (1990)8:135; Kunze et al., *J. Basic Microbiol.* (1985)25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284–289; Tilburn et al., *Gene* (1983) 26:205–221; Yelton et al., *Proc. Natl. Acad. Sci.* (*USA*) (1984) 81:1470–1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765–776; Miller et al., *Ann. Rev. Microbiol.* (1988) 42:177; Carbonell et al., *Gene* (1988) 73:409; Maeda et al., *Nature* (1985) 315:592–594; Lebacq-Verheyden et al., *Mol. Cell. Biol.* (1988) 8:3129; Smith et al., *Proc. Natl. Acad. Sci.* (*USA*) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47–55, Miller et al., *Generic Engineering* (1986) 8:277–279, and Maeda et al., *Nature* (1985) 315:592–594.

Mammalian Cells. Mammalian expression is accomplished as described in Dijkema et al., *EMBO J.* (1985) 4:761, Gorman et al., *Proc. Natl. Acad. Sci.* (*USA*) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. Pat. No. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated-in the cell to which the gene is native. For example, an endogenous gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference. As such, also encompassed in the subject invention is the production of the subject polymorphic DGAT proteins without manipulation of the encoding nucleic acid itself, but instead through integration of a regulatory sequence into the genome of cell that already includes a gene encoding the desired protein, as described in the above incorporated patent documents.

Antibodies Specific for Polymorphic DGAT Polypeptides

The invention further provides antibodies, particularly isolated antibodies, that are specific for polymorphic DGAT polypeptides of the invention. The antibodies of the invention are useful in a variety of diagnostic assays, as described in further detail below. For example, an antibody of the invention can be used to detect a polymorphic DGAT polypeptide in a biological sample.

Isolated polymorphic DGAT polypeptides of the invention are useful for the production of antibodies, where short fragments provide for antibodies specific for the particular polypeptide, and larger fragments or the entire protein allow for the production of antibodies over the surface of the polypeptide. Accordingly, the invention provides isolated antibodies which specifically bind a polymorphic DGAT polypeptide, or antigenic fragment thereof. Antibodies may be raised to the wild-type or variant forms. Antibodies may be raised to isolated peptides corresponding to these domains, or to the native protein. Antibodies may be raised to polypeptides and/or peptide fragments of polymorphic DGAT from any mammalian species.

Particularly useful are antibodies that distinguish between or among DGAT polymorphic polypeptides. Antibodies may be generated that specifically recognize a DGAT polypeptide comprising one or more specific polymorphisms. Generation of such antibodies, and determination of their specificity relative to other DGAT polypeptides, is readily accomplished by those skilled in the art using conventional methods and assays. As one non-limiting example, an enzyme-linked immunosorbent assay (ELISA) can be used to determine the specificity of a given monoclonal antibody for a particular polymorphic DGAT polypeptide.

The polymorphic DGAT polypeptides of the invention are useful for the production of antibodies, where short fragments provide for antibodies specific for the particular polypeptide, and larger fragments or the entire protein allow for the production of antibodies over the surface of the polypeptide. As used herein, the term "antibodies" includes antibodies of any isotype, fragments of antibodies which retain specific binding to antigen, including, but not limited to, Fab, Fv, scFv, and Fd fragments, fusion proteins comprising such antibody fragments, detectably labeled antibodies, and chimeric antibodies. "Antibody specificity", in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens. Methods of determining specific antibody binding are well known to those skilled in the art, and can be used to determine the specificity of antibodies of the invention for a polymorphic DGAT polypeptide.

Antibodies are prepared in accordance with conventional ways, where the expressed is polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in $E.\ coli,$ and the heavy and light chains mixed to further enhance the affinity of the antibody. Alternatives to in vivo immunization as a method of raising antibodies include binding to phage display libraries, usually in conjunction with in vitro affinity maturation.

Antibodies may be attached, directly or indirectly (e.g., via a linker molecule) to a solid support for use in a diagnostic assay to determine and/or measure the presence of a polymorphic DGAT polypeptide in a biological sample. Attachment is generally covalent, although it need not be. Solid supports include, but are not limited to, beads (e.g., polystyrene beads, magnetic beads, and the like); plastic surfaces (e.g., polystyrene or polycarbonate multi-well plates typically used in an ELISA or radioimmunoassay (RIA), and the like); sheets, e.g., nylon, nitrocellulose, and the like; and chips, e.g., $SiO_2$ chips such as those used in microarrays. Accordingly, the invention further provides assay devices comprising antibodies attached to a solid support.

A single antibody or a battery of different antibodies can then be used to create an assay device. Such an assay device can be prepared using conventional technology known to those skilled in the art. The antibody can be purified and isolated using known techniques and bound to a support surface using known procedures. The resulting surface having antibody bound thereon can be used to assay a test sample, e.g., a biological sample, in vitro to determine if the sample contains one or more types of DGAT polymorphic polypeptides. For example, antibodies which bind only to a specific DGAT polymorphic epitope can be attached to the surface of a material. Alternatively, a plurality of specific antibodies, which may be arranged in an array, wherein antibodies specific for two or more different DGAT polymorphic epitopes are attached to the solid support, can be used. A test sample is brought into contact with the antibodies bound to the surface of material. Specific binding can be detected using any known method. If specific binding is not detected, it can be deduced that the sample does not contain the specific DGAT polymorphic epitope. As one non-limiting example of how specific binding can be detected, once the test sample has been contacted with the antibodies bound to the solid support, a second, detectably-labeled antibody can be added, which recognizes a DGAT epitope distinct from the epitope recognized by the solid support-bound antibody.

A variety of other reagents may be included in the assays to detect DGAT polymorphic polypeptides described herein. These include reagents such as salts, neutral proteins, e.g. albumin, detergents, etc., that are used to facilitate optimal protein-protein binding, and/or reduce non-specific or background interactions. Reagents that improve the efficiency of the assay, such as protease inhibitors, anti-microbial agents, etc. may be used. The components are added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hours will be sufficient.

Compositions

The present invention further provides compositions, including pharmaceutical compositions, comprising the polypeptides, polynucleotides, antibodies, recombinant vectors, and host cells of the invention. These compositions may include a buffer, which is selected according to the desired use of the polypeptide, antibody, polynucleotide, recombinant vector, or host cell, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, A. Gennaro (1995) "Remington: The Science and Practice of Pharmacy", 19th edition, Lippincott, Williams, & Wilkins.

Diagnostic Assays

Isolated DGAT polymorphic nucleic acid molecules of the invention are useful in diagnostic assays. The present invention provides diagnostic methods for detecting, in a nucleic acid sample from an individual, a DGAT polymorphism associated with a condition associated with DGAT activity. The detection methods are useful in methods for identifying individuals predisposed to developing a condition associated with DGAT activity, as well as in methods for genetically diagnosing a condition associated with DGAT activity.

The invention further provides methods for detecting the presence of and/or a level of DGAT mRNA in a biological sample; and methods for detecting the presence of and/or a level of polymorphic DGAT polypeptide in a biological sample.

Thus, in some embodiments, a method is provided for detecting, in a polynucleotide sample derived from an individual, the presence of DGAT polymorphism associated with a disorder associated with DGAT activity in an individual, which method comprises analyzing a polynucleotide sample from an individual for the presence of a nucleotide sequence polymorphism in a DGAT gene, wherein the nucleotide sequence polymorphism is associated with a condition relating to abnormal fat storage.

In other embodiments, a method is provide for detecting a level of DGAT mRNA in a biological sample derived from an individual, comprising analyzing a polynucleotide sample from an individual for the level of DGAT polypeptide-encoding mRNA. The level of DGAT mRNA may be associated with a condition relating to DGAT activity.

In other embodiments, a method is provided for detecting a propensity of an individual to develop a condition associated with DGAT activity, comprising analyzing a polynucleotide sample derived from the individual for the presence of a polymorphism in a DGAT gene, wherein said DGAT-gene polymorphism is associated with a condition associated with DGAT activity.

In other embodiments, a method is provided for genetically diagnosing a condition associated with DGAT activity, comprising analyzing a polynucleotide sample from said individual for the presence of a polymorphism in a diacylglycerol acyltransferase (DGAT) gene, wherein said DGAT gene polymorphism is associated with a condition associated with DGAT activity.

In still other embodiments, a method is provided for detecting the presence of and/or the level of a polymorphic DGAT polypeptide in a biological sample. In further embodiments, a method is provided for detecting the presence of and/or the level of an enzymatic activity of a polymorphic DGAT polypeptide in a biological sample.

Polynucleotide samples derived from (e.g., obtained from) an individual are obtained from a biological sample taken from the individual. Any biological sample that comprises a polynucleotide from the individual is suitable for use in the methods of the invention. The biological sample may be processed so as to isolate the polynucleotide. Alternatively, whole cells or other biological samples may be used without isolation of the polynucleotides contained therein. Detection of a DGAT polymorphism that is associated with a disorder associated with DGAT activity in a polynucleotide sample derived from an individual can be accomplished by any means known in the art, including, but not limited to, amplification of a sequence with specific primers; determination of the nucleotide sequence of the polynucleotide sample; hybridization analysis; single strand conformational polymorphism analysis; denaturing gradient gel electrophoresis; mismatch cleavage detection; and the like. Detection of a DGAT polymorphism that is associated with a condition associated with DGAT activity can also be accomplished by detecting an alteration in the level of a mRNA transcript of a DGAT gene; aberrant modification of a DGAT gene, e.g., an aberrant methylation pattern; the presence of a non-wild-type splicing pattern of DGAT mRNA; an alteration in the level of DGAT polypeptide; and/or an alteration in DGAT polypeptide enzymatic activity.

Detection of a DGAT polymorphism by analyzing a polynucleotide sample can be conducted in a number of ways. A test nucleic acid sample can-be amplified with primers which amplify a region known to comprise a DGAT polymorphism(s). Non-limiting examples of such primers are provided in Example 1. Genomic DNA or mRNA can be used directly. Alternatively, the region of interest can be cloned into a suitable vector and grown in sufficient quantity for analysis. The nucleic acid may be amplified by conventional techniques, such as a polymerase chain reaction (PCR), to provide sufficient amounts for analysis. The use of the polymerase chain reaction is described in a variety of publications, including, e.g., "PCR Protocols (Methods in Molecular Biology)" (2000) J. M. S. Bartlett and D. Stirling, eds, Humana Press; and "PCR Applications: Protocols for Functional Genomics" (1999) Innis, Gelfand, and Sninsky, eds., Academic Press. Once the region comprising a DGAT polymorphism has been amplified, the DGAT polymorphism can be detected in the PCR product by nucleotide sequencing, by SSCP analysis, or any other method known in the art. In performing SSCP analysis, the PCR product may be digested with a restriction endonuclease that recognizes a sequence within the PCR product generated by using as a template a reference DGAT sequence, but does not recognize a corresponding PCR product generated by using as a template a variant DGAT sequence by virtue of the fact that the variant sequence no longer contains a recognition site for the restriction endonuclease. Examples of this approach are provided in Example 2.

PCR may also be used to determine whether a polymorphism is present by using a primer that is specific for the polymorphism. Such methods may comprise the steps of collecting from an individual a biological sample comprising the individual's genetic material as template, optionally isolating template nucleic acid (genomic DNA, mRNA, or both) from the biological sample, contacting the template nucleic acid sample with one or more primers that specifically hybridize with a DGAT polymorphic nucleic acid molecule under conditions such that hybridization and amplification of the template nucleic acid molecules in the sample occurs, and detecting the presence, absence, and/or relative amount of an amplification product and comparing tie length to a control sample. Observation of an amplification product of the expected size is an indication that the DGAT polymorphism contained within the DGAT polymorphic primer is present in the test nucleic acid sample. Parameters such as hybridization conditions, DGAT polymorphic primer length, and position of the polymorphism within the DGAT polymorphic primer may be chosen such that hybridization will not occur unless a polymorphism present in the primer(s) is also present in the sample nucleic acid. Those of ordinary skill in the art are well aware of how to select and vary such parameters. See, e.g., Saiki et al. (1986) *Nature* 324:163; and Saiki et al (1989) *Proc. Natl. Acad. Sci. USA* 86:6230. As one non-limiting example, a PCR primer comprising the T78C variation described in Example 1 may be used.

Alternatively, various methods are known in the art that utilize oligonucleotide ligation as a means of detecting polymorphisms. See, e.g., Riley et al. (1990) *Nucleic Acids Res.* 18:2887–2890; and Delahunty et al. (1996) *Am. J Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid may be sequenced by a dideoxy chain termination method or other well-known methods. Genomic DNA or mRNA may be used directly. If mRNA is used, a cDNA copy may first be made. If desired, the sample nucleic acid can be amplified using a PCR. A variety of sequencing reactions known in the art can be used to directly sequence the DGAT gene, or a portion thereof in which a specific polymorphism is known to occur, and detect polymorphisms by comparing the sequence of the sample nucleic acid with a reference polynucleotide that contains a DGAT polymorphism. Any of a variety of automated sequencing procedures can be used. See, e.g., WO 94/16101; Cohen et al. (1996) Adv. Chromatography 36:127–162.

Hybridization with the variant sequence may also be used to determine the presence of a DGAT polymorphism. Hybridization analysis can be carried out in a number of different ways, including, but not limited to Southern blots, Northern blots, dot blots, microarrays, etc. The hybridization pattern of a control and variant sequence to an array of oligonucleotide probes immobilized on a solid support, as described in U.S. Pat No. 5,445,934, or in WO 95/35505, may also be used as a means of detecting the presence of variant sequences. Identification of a polymorphism in a nucleic acid sample can be performed by hybridizing a sample and control nucleic acids to high density arrays containing hundreds or thousands of oligonucleotide probes. Cronin et al. (1996) Human Mutation 7:244–255; and Kozal et al. (1996) Nature Med. 2:753–759.

Single strand conformational polymorphism (SSCP) analysis; denaturing gradient gel electrophoresis (DGGE); mismatch cleavage detection; and heteroduplex analysis in gel matrices can also be used to detect polymorphisms. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels. The aforementioned techniques are well known in the art. Detailed description of these techniques can be found in a variety of publications, including, e.g., "Laboratory Methods for the Detection of Mutations and Polymorphisms in DNA" (1997) G. R. Taylor, ed., CRC Press, and references cited therein.

A number of methods are available for determining the expression level of a polymorphic DGAT nucleic acid molecule, e.g., a polymorphic DGAT mRNA, or polymorphic DGAT polypeptide in a particular sample. Diagnosis may be performed by a number of methods to determine the absence or presence or altered amounts of normal or abnormal DGAT mRNA in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc. The presence and/or the level of a polymorphic DGAT polypeptide may also be detected and/or quantitated in any Alternatively, one may focus on the expression of DGAT mRNA. Biochemical studies may be performed to determine whether a sequence polymorphism in a DGAT coding region or control regions is associated with disease. Disease associated polymorphisms may include deletion or truncation of the gene, mutations that alter expression level, that affect the activity of the protein, etc.

Changes in the promoter or enhancer sequence that may affect expression levels of DGAT can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

Screening for mutations in a polymorphic DGAT polypeptide may be based on the functional or antigenic characteristics of the protein. Protein truncation assays are useful in detecting deletions that may affect the biological activity of the protein. Various immunoassays designed to detect polymorphisms in polymorphic DGAT polypeptides may be used in screening. Where many diverse genetic mutations lead to a particular disease phenotype, functional protein assays have proven to be effective screening tools. The activity of the encoded a polymorphic DGAT polypeptide may be determined by comparison with a reference DGAT polypeptide lacking a specific polymorphism.

Diagnostic methods of the subject invention in which the level of DGAT gene expression is of interest will typically involve comparison of the DGAT nucleic acid abundance of a sample of interest with that of a control value to determine any relative differences, where the difference may be measured qualitatively and/or quantitatively, which differences are then related to the presence or absence of an abnormal DGAT gene expression pattern. A variety of different methods for determine the nucleic acid abundance in a sample are known to those of skill in the art, where particular methods of interest include those described in: Pietu et al., Genome Res. (June 1996) 6: 492–503; Zhao et al., Gene (Apr. 24, 1995) 156: 207–213; Soares, Curr. Opin. Biotechnol. (October 1997) 8: 542–546; Raval, J. Pharmacol Toxicol Methods (November 1994) 32: 125–127; Chalifour et al., Anal. Biochem (Feb. 1, 1994) 216: 299–304; Stolz & Tuan, Mol. Biotechnol. (December 19960 6: 225–230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

Monitoring Effects of Drug Treatment

Monitoring the influence of agents (e.g., drugs, compounds) on the expression or activity of a DGAT protein (e.g., modulation of transcriptional activation) can be applied not only in basic drug screening, but also in clinical trials. For example, the effectiveness of an agent determined by a screening assay as described herein to increase DGAT gene expression, protein levels, or upregulate DGAT activity, can be monitored in clinical trials of subjects exhibiting decreased DGAT gene expression, protein levels, or down-regulated DGAT activity. Alternatively, the effectiveness of an agent determined by a screening assay to decrease DGAT gene expression, protein levels, or down-regulate DGAT activity, can be monitored in clinical trials of subjects exhibiting increased DGAT gene expression, protein levels, or upregulated DGAT activity. In such clinical trials, the expression or activity of a DGAT gene, and preferably, other genes that have been implicated in, for example, a disorder associated with DGAT activity can be used as a "read out" or markers of the phenotype of a particular cell.

For example, and not by way of limitation, genes, including DGAT, that are modulated in cells by treatment with an agent (e.g., compound, drug or small molecule) which modulates DGAT activity (e.g., identified in a screening assay as described herein) can be identified. Thus, to study the effect of agents on fat storage disorders, for example, in a clinical trial, cells can be isolated and RNA prepared and analyzed for the levels of expression of DGAT and other genes implicated in a disorder associated with DGAT activity. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of DGAT or other genes. In this way, the gene expression pattern can serve as a marker, indicative of the physiological response of the cells to the agent. Accordingly, this response state may be determined before, and at various points during treatment of the individual with the agent.

In some embodiments, the present invention provides a method for monitoring the effectiveness of treatment of a subject with an agent (e.g., an agonist, antagonist, peptidomimetic, protein, peptide, nucleic acid, small molecule, or other drug that modifies a DGAT activity) comprising the steps of (i) obtaining a pre-administration sample from a subject prior to administration of the agent; (ii) detecting the level of expression of a DGAT protein, mRNA, or genomic DNA in the pre-administration sample; (iii) obtaining one or more post-administration samples from the subject, (iv) detecting the level of expression or activity of the DGAT protein, mRNA, or genomic DNA in the post-administration samples; (v) comparing the level of expression or activity of the DGAT protein, mRNA, or genomic DNA in the pre-administration sample with the DGAT protein, mRNA, or genomic DNA in the post administration sample or samples; and (vi) altering the administration of the agent to the subject accordingly. For example, increased administration of the agent may be desirable to increase the expression or activity of DGAT to higher levels than detected, i.e., to increase the effectiveness of the agent. Alternatively, decreased administration of the agent may be desirable to decrease expression or activity of DGAT to lower levels than detected, i.e. to decrease the effectiveness of the agent. According to such an embodiment, DGAT expression or activity may be used as an indicator of the effectiveness of an agent, even in the absence of an observable phenotypic response.

Linkage Analysis: Diagnostic screening may be performed for polymorphisms that are genetically linked to a phenotypic variant in DGAT activity or expression, particularly through the use of microsatellite markers or single nucleotide polymorphisms (SNP). The microsatellite or SNP polymorphism itself may not phenotypically expressed, but is linked to sequences that result in altered activity or expression. Two polymorphic variants may be in linkage disequilibrium, i.e. where alleles show non-random associations between genes even though individual loci are in Hardy-Weinberg equilibrium.

Linkage analysis may be performed alone, or in combination with direct detection of phenotypically evident polymorphisms. The use of microsatellite markers for genotyping is well documented. For examples, see Mansfield et al. (1994) *Genomics* 24:225–233; and Ziegle et al. (1992) *Genomics* 14:1026–1031. The use of SNPs for genotyping is illustrated in Underhill et al. (1996) *Proc. Natl. Acad. Sci. USA* 93:196–200.

Genetic linkage maps show the relative locations of specific DNA markers along a chromosome. Any inherited physical or molecular characteristic that differs among individuals and is easily detectable in the laboratory is a potential genetic marker. DNA sequence polymorphisms are useful markers because they are plentiful and easy to characterize precisely. Many such polymorphisms are located in non-coding regions and do not affect the phenotype of the organism, yet they are detectable at the DNA level and can be used as markers. Examples include restriction fragment length polymorphisms (RFLPs), which reflect sequence variations in DNA sites or differences in the length of the product, which can be cleaved by DNA restriction enzymes, microsatellite markers, which are short repeated sequences that vary in the number of repeated units, single nucleotide polymorphisms (SNPs), and the like.

The "linkage" aspect of the map is a measure of how frequently two markers are inherited together. The closer the markers are to each other physically, the less likely a recombination event will fall between and separate them. Recombination frequency thus provides an estimate of the distance between two markers. The value of the genetic map is that an inherited trait can be located on the map by following the inheritance of a DNA marker present in affected individuals, but absent in unaffected individuals, even though the molecular basis for the trait may not yet be understood. Genetic maps have been used to find the exact chromosomal location of several important disease genes, including cystic fibrosis, muscular dystrophy, sickle cell disease, Tay-Sachs disease, fragile X syndrome and many others.

An emerging class of marker for genetic analysis of the single nucleotide polymorphism, and other simple polymorphisms, e.g. deletions, double nucleotide polymorphisms, etc. SNPs are generally biallelic systems, that is, there are two alleles that a population may have for any particular marker. This means that the information content per SNP marker is relatively low when compared to microsatellite markers, which may have upwards of 10 alleles. SNPs also tend to be very population-specific; a marker that is polymorphic in one population may not be very polymorphic in another.

SNP markers offer a number of benefits that will make them an increasingly valuable tool. SNPs, found approximately every kilobase (see Wang et al. (1998) *Science* 280:1077–1082), offer the potential for generating very high density genetic maps, which will be extremely useful for developing haplotyping systems for genes or regions of interest, and because of the nature of SNPs, they may in fact be the polymorphisms associated with the disease phenotypes under study. The low mutation rate of SNPs also makes them excellent markers for studying complex genetic traits.

Substrate screening assay. Substrate screening assays are used to determine the catalytic activity of a DGAT protein or peptide fragment on a substrate. Many suitable assays are known in the art, including the use of primary or cultured cells, genetically modified cells (e g., where DNA encoding the DGAT polymorphism to be studied is introduced into the cell within an artificial construct), cell-free systems, e.g. microsomal preparations or recombinantly produced enzymes in a suitable buffer, or in animals, including human clinical trials.

Typically a detectably labeled substrate is input into the assay system, and the generation of labeled triglyceride is measured over time. The choice of detection system is determined by the substrate and the specific assay parameters. Assays are conventionally run, and will include negative and positive controls, varying concentrations of substrate and enzyme, etc. Exemplary assays may be found in the literature, as described above.

Pharmacokinetic parameters. Pharmacokinetic parameters provide fundamental data for designing safe and effective dosage regimens. A drug's volume of distribution, clearance, and the derived parameter, half-life, are particularly important, as they determine the degree of fluctuation between a maximum and minimum plasma concentration during a dosage interval, the magnitude of steady state concentration and the time to reach steady state plasma concentration upon chronic dosing. Parameters derived from in vivo drug administration are useful in determining the clinical effect of a particular DGAT genotype.

Expression assay. An assay to determine the effect of a sequence polymorphism on DGAT expression. Expression assays may be performed in cell-free extracts, or by transforming cells with a suitable vector. Alterations in expression may occur in the basal level that is expressed in one or more cell types, or in the effect that an expression modifier has on the ability of the gene to be inhibited or induced. Expression levels of a variant alleles are compared by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

Gel shift or electrophoretic mobility shift assay provides a simple and rapid method for detecting DNA-binding proteins (Ausubel, F.M. et al. (1989) In: Current Protocols in Molecular Biology, Vol. 2, John Wiley and Sons, New York). This method has been used widely in the study of sequence-specific DNA-binding proteins, such as transcription factors. The assay is based on the observation that complexes of protein and DNA migrate through a nondenaturing polyacrylamide gel more slowly than free DNA fragments or double-stranded oligonucleotides. kilo The gel shift assay is performed by incubating a purified protein, or a complex mixture of proteins (such as nuclear or cell extract preparations), with an end-labeled DNA fragment containing the putative protein binding site. The reaction products are then analyzed on a nondenaturing polyacrylamide gel. The specificity of the DNA-binding protein for the putative binding site is established by competition experiments using DNA fragments or oligonucleotides containing a binding site for the protein of interest, or other unrelated DNA sequences.

Expression assays can be used to detect differences in expression of polymorphisms with respect to tissue specificity, expression level, or expression in response to exposure to various substrates, and/or timing of expression during development.

Genotyping DGAT genotyping is performed by DNA or RNA sequence and/or hybridization analysis of any convenient sample from a patient, e.g. biopsy material, blood sample (serum, plasma, etc.), buccal cell sample, etc. A nucleic acid sample from an individual is analyzed for the presence of polymorphisms in DGAT, particularly those that affect the activity or expression of DGAT. Specific sequences of interest include any polymorphism that leads to changes in basal expression in one or more tissues, to changes in the modulation of DGAT expression by modifiers, or alterations in DGAT substrate specificity and/or activity.

The effect of a polymorphism in the DGAT gene sequence on the response to a particular substrate or modifier of DGAT is determined by in vitro or in vivo assays. Such assays may include monitoring the metabolism of a substrate during clinical trials to determine the DGAT enzymatic activity, specificity or expression level. Generally, in vitro assays are useful in determining the direct effect of a particular polymorphism, while clinical studies will also detect an enzyme phenotype that is genetically linked to a polymorphism.

The response of an individual to the substrate or modifier can then be predicted by determining the DGAT genotype, with respect to the polymorphism. Where there is a differential distribution of a polymorphism by racial background, guidelines for drug administration can be generally tailored to a particular ethnic group.

The basal expression level in different tissue may be determined by analysis of tissue samples from individuals typed for the presence or absence of a specific polymorphism. Any convenient method may be use, e.g. ELISA, RIA, etc. for protein quantitation, northern blot or other hybridization analysis, quantitative RT-PCR, etc. for mRNA quantitation. The tissue specific expression is correlated with the genotype.

The alteration of DGAT expression in response to a modifier is determined by administering or combining the candidate modifier with an expression system, e.g. animal, cell, in vitro transcription assay, etc. The effect of the modifier on DGAT transcription and/or steady state mRNA levels is determined. As with the basal expression levels, tissue specific interactions are of interest. Correlations are made between the ability of an expression modifier to affect DGAT activity, and the presence of the provided polymorphisms. A panel of different modifiers, cell types, etc. may be screened in order to determine the effect under a number of different conditions.

A DGAT polymorphism that results in altered enzyme activity or specificity is determined by a variety of assays known in the art. The enzyme may be tested for formation of triglyceride product in vitro, for example in defined buffer, or in cell or subcellular lysates, where the ability of a substrate to be acted on by DGAT under physiologic conditions is determined. Where there are not significant issues of toxicity from the substrate or products(s), in vivo human trials maybe utilized, as previously described.

The genotype of an individual is determined with respect to the provided DGAT gene polymorphisms. The genotype is useful for determining the presence of a phenotypically evident polymorphism, and for determining the linkage of a polymorphism to phenotypic change.

Any of a number of techniques known to those skilled in the art can be used to detect a polymorphism in a DGAT gene, using an isolated polynucleotide of the invention. These include, but are not limited to, direct sequencing of the interval from affected individuals (Chadwick et al.

(1996) *Biotechniques* 20:676–683); and hybridization with one or more probes derived from a region of a DGAT gene, including allele-specific oligonucleotide hybridization (Wong and Senadheera (1997) *Clin. Chem.* 43:1857–1861). The region being detected can optionally be amplified by known techniques, including, but not limited to, a polymerase chain reaction. Other analytical techniques include, but are not limited to, single-strand conformation analysis; restriction length polymorphism (RFLP) analysis; enzymatic mismatch cleavage techniques such as glycosylase mediated polymorphism detection (Vaughan and McCarthy (1998) *Nucl. Acids Res.* 26:810–815); heteroduplex PCR (Deuter and Muller (1998) *Hum. Mutat.* 11:84–89); and fiberoptic DNA sensor array techniques (Healey et al. (1997) *Anal. Biochem.* 251:270–279). Automated methods of detecting polymorphisms have been developed and can be used in the methods of the present invention. See, for example, Marshall and Hodgson (1998) *Nature Biotechnol.* 16:27–31. Other methods include, for example, PCR-RFLP. Hani et al. (1998) *J. Clin. Invest.* 101:521–526.

Treatment Methods

The present invention hither provides a method of treating an individual clinically diagnosed with a condition associated with DGAT activity. The methods generally comprises analyzing a polynucleotide sample from an individual clinically diagnosed with a condition associated with DGAT activity for the presence or absence of a diacylglycerol acyltransferase (DGAT) gene polymorphism. The presence of a DGAT gene polymorphism associated with a condition relating to abnormal fat storage confirms the clinical diagnosis of a condition associated with DGAT activity. A treatment plan that is most effective for individuals clinically diagnosed as having a condition associated with DGAT activity is then selected on the basis of the detected DGAT polymorphism. Genotype information obtained as described above can be used to predict the response of the individual to a particular DGAT substrate (e.g., activator or inhibitor of DGAT enzymatic activity), or modifier of DGAT gene expression. Thus, the invention further provides a method for predicting a patient's likelihood to respond to a drug treatment for a condition associated with DGAT activity, comprising determining a patient's genotype in a DGAT gene, wherein the presence of a DGAT allele associated with a condition associated with DGAT activity is predictive of the patient's likelihood to respond to a drug treatment for the condition. Where an expression modifier inhibits DGAT expression, then drugs that are a DGAT substrate will be metabolized more slowly if the modifier is co-administered. Where an expression modifier induces DGAT expression, a co-administered substrate will typically be metabolized more rapidly. Similarly, changes in DGAT activity will affect the metabolism of an administered drug. The pharmacokinetic effect of the interaction will depend on the metabolite that is produced, e.g. a prodrug is metabolized to an active form, a drug is metabolized to an inactive form, an environmental compound is metabolized to a toxin, etc. Consideration is given to the route of administration, drug-drug interactions, drug dosage, etc.

Thus, another aspect of the invention provides methods for tailoring an individual's prophylactic. or therapeutic treatment with DGAT expression and/or activity modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Agents that have a stimulatory or inhibitory effect on DGAT expression levels or DGAT enzymatic activity can be administered to individuals to treat (prophylactically or therapeutically) disorders associated with DGAT activity. Additionally, the isolated polymorphic DGAT nucleic acid molecules of the present invention, as well as agents, or modulators which have a stimulatory or inhibitory effect on DGAT expression levels or DGAT enzymatic activity can be administered to individuals to treat a condition associated with DGAT activity. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a modulator of DGAT expression or enzymatic activity ("a DGAT modulator") as well as tailoring the dosage and/or therapeutic regimen of treatment with a DGAT modulator.

Determination of how a given DGAT polymorphism is predictive of a patient's likelihood of responding to a given drug treatment for a condition relating to abnormal fat storage can be accomplished by determining the genotype of the patient in the DGAT gene, as described above, and/or determining the effect of the drug on DGAT gene expression, and/or determining the effect of the drug on DGAT enzymatic activity. Information generated from one or more of these approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a DGAT molecule or DGAT modulator, such as a modulator identified by one of the exemplary screening assays described herein.

Microarrays

The invention further provides an array of oligonucleotides (also referred to herein as "probes"), where discrete positions on the array are complementary to one or more of the provided polymorphic sequences, e.g. oligonucleotides of at least 12 nt, at least about 15 nt, at least about 18 nt, at least about 20 nt, or at least about 25 nt, or longer, and including the sequence flanking the polymorphic position. Such an array may comprise a series of oligonucleotides, each of which can specifically hybridize to a different polymorphism. For examples of arrays, see Hacia et al. (1996) *Nat. Genet.* 14:441–447 and DeRisi et al. (1996) *Nat. Genet.* 14:457–460.

An array may include all or a subset of the polymorphisms listed in Example 1. One or more polymorphic forms may be present in the array. In some embodiments, an array includes at least 2 different polymorphic sequences, i.e. polymorphisms located at unique positions within the locus, and may include as many all of the provided polymorphisms. Arrays of interest may further comprise sequences, including polymorphisms, of other genetic sequences, particularly other sequences of interest for pharmacogenetic screening, including, but not limited to, other genes associated with obesity and/or other gene mutations associated with obesity, including, but not limited to LEP or obese or LEP (leptin), diabetes (leptin receptor), fat (carboxypeptidase E), tubby (tubby protein), LDLR (low density lipoprotein receptor), MC3R-MC35R (melanocortin receptors 3–5), etc, or an equivalent thereof in another species. The oligonucleotide sequence on the array is generally at least about 12 nt in length, at least about 15 nt, at least about 18 nt, at least about 20 nt, or at least about 25 nt, or may be the length of the provided polymorphic sequences, or may extend into the flanking regions to generate fragments of 100 to 200 nt in length. For examples of arrays, see Ramsay (1998) *Nature Biotech.* 16:40–44; Hacia et al (1996) *Nature Genetics* 14:441–447; Lockhart et al (1996) *Nature Biotechnol.* 14:1675–1680; and De Risi et al. (1996) *Nature Genetics* 14:457–460.

A number of methods are available for creating microarrays of biological samples, such as arrays of DNA samples to be used in DNA hybridization assays. Exemplary are PCT Application Serial. No. WO95/35505, published Dec. 28,1995; U.S. Pat. No. 5,445,934, issued Aug. 29, 1995; and Drnanac et al. (1993) *Science* 260:1649–1652. Yershov et al, (1996) *Genetics* 93:4913–4918 describe an alternative construction of an oligonucleotide array. The construction and use of oligonucleotide arrays is reviewed by Ramsay (1998) supra.

Methods of using high density oligonucleotide arrays are known in the art. For example, Milosavljevic et al. (1996) *Genomics* 37:77–86 describe DNA sequence recognition by hybridization to short oligomers. See also, Drmanac et al. (1998) *Nature Biotech.* 16:54–58; and Drnanac and Drmanac (1999) *Methods Enzymol.* 303:165–178; The use of arrays for identification of unknown mutations is proposed by Ginot (1997) *Human Mutation* 10:1–10.

Detection of known mutations is described in Hacia et al. (1996) *Nat. Genet.* 14:441–447; Cronin et al. (1996) *Human Mut.* 7:244–255;, and others. The use of arrays in genetic mapping is discussed in Chee et al. (1996) *Science* 274:610–613; Sapolsky and Lishutz (1996) *Genomics* 33:445–456; etc. Shoemaker et al. (1996) *Nat. Genet.* 14:450–456 perform quantitative phenotypic analysis of yeast deletion mutants using a parallel bar-coding strategy.

Quantitative monitoring of gene expression patterns with a complementary DNA microarray is described in Schena et al. (1995) *Science* 270:467. DeRisi et al (1997) *Science* 270:680–686 explore gene expression on a genomic scale. Wodicka et al. (1997) *Nat. Biotech.* 15:1–15 perform genome wide expression monitoring in *S. cerevisiae.*

A DNA sample is prepared in accordance with conventional methods, e.g. lysing cells, removing cellular debris, separating the DNA from proteins, lipids or other components present in the mixture and then using the isolated DNA for cleavage. See Molecular Cloning, A Laboratory Manual, 2nd ed. (eds. Sambrook et al.) CSH Laboratory Press, Cold Spring Harbor, N.Y. 1989. Generally, at least about 0.5 $\mu$g of DNA will be employed, usually at least about 5 $\mu$g of DNA, while less than 50 $\mu$g of DNA will usually be sufficient.

The nucleic acid samples are cleaved to generate probes. It will be understood by one of skill in the art that any method of random cleavage will generate a distribution of fragments, varying in the average size and standard deviation. Usually the average size will be at least about 12 nucleotides in length, more usually at least about 20 nucleotides in length, and preferably at least about 35 nucleotides in length. Where the variation in, size is great, conventional methods may be used to remove the large and/or small regions of the fragment population.

It is desirable, but not essential to introduce breaks randomly, with a method which does not act preferentially on specific sequences. Preferred methods produce a reproducible pattern of breaks. Methods for introducing random breaks or nicks in nucleic acids include reaction with Fenton reagent to produce hydroxyl radicals and other chemical cleavage systems, integration mediated by retroviral integrase, partial digestion with an ultra-frequent cutting restriction enzymes, partial digestion of single stranded with S1 nuclease, partial digestion with DNAse I in the absence or presence of $Mn^{++}$, etc.

The fragmented nucleic acid samples are denatured and labeled. Labeling can be performed according to methods well known in the art, using any method that provides for a detectable signal either directly or indirectly from the nucleic acid fragment. In a preferred embodiment, the fragments are end-labeled, in order to minimize the steric effects of the label. For example, terminal transferase may be used to conjugate a labeled nucleotide to the nucleic acid fragments. Suitable labels include biotin and other binding moieties; fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), and the like. Where the label is a binding moiety, the detectable label is conjugated to a second stage reagent, e.g. avidin, streptavidin, etc. that specifically binds to the binding moiety, for example a fluorescent probe attached to streptavidin. Incorporation of a fluorescent label using enzymes such as reverse transcriptase or DNA polymerase, prior to fragmentation of the sample, is also possible.

Each of the labeled genome samples is separately hybridized to an array of oligonucleotide probes. Hybridization of the labeled sequences is accomplished according to methods well known in the art. Hybridization can be carried out under conditions varying in stringency, preferably under conditions of high stringency, e.g. 6×SSPE, at 65° C., to allow for hybridization of complementary sequences having extensive homology, usually having no more than one or two mismatches in a probe of 25 nucleotides in length, i.e. at least 95% to 100% sequence identity.

High density microarrays of oligonucleotides are known in the art and are commercially available. The sequence of oligonucleotides on the array will correspond to the known target sequences of one of the genomes, as previously described. Arrays of interest for the subject methods will generally comprise at least about $10^3$ different sequences, usually at least about $10^4$ different sequences, and may comprise $10^5$ or more different sequences. The length of oligonucleotide present on the array is an important factor in how sensitive hybridization will be to the presence of a mismatch. Usually oligonucleotides will be at least about 12 nt in length, more usually at least about 15 nt in length, preferably at least about 20 nt in length and more preferably at least about 25 nt in length, and will be not longer than about 35 nt in length, usually not more than about 30 nt in length.

Methods of producing large arrays of oligonucleotides are described in U.S. Pat. No. 5,134,854 (Pirrung et al.), and U.S. Pat. No. 5,445,934 (Fodor et al.) using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in International Patent application WO 95/35505.

Microarrays can be scanned to detect hybridization of the labeled genome samples. Methods and devices for detecting fluorescently marked targets on devices are known in the art. Generally such detection devices include a microscope and light source for directing light at a substrate. A photon counter detects fluorescence from the substrate, while an x-y translation stage varies the location of the substrate. A confocal detection device that may be used in the subject methods is described in U.S. Pat. No. 5,631,734. A scanning laser microscope is described in Shalon et al. (1996) *Genome Res.* 6:639. A scan, using the appropriate excitation line, is performed for each fluorophore used. The digital images generated from the scan are then combined for subsequent analysis. For any particular array element, the ratio of the fluorescent signal from one Nucleic acid sample is compared to the fluorescent signal from the other Nucleic acid sample, and the relative signal intensity determined.

Methods for analyzing the data collected by fluorescence detection are known in the art. Data analysis includes the steps of determining fluorescent intensity as a function of substrate position from the data collected, removing outliers, i.e. data deviating from a predetermined statistical distribution, and calculating the relative binding affinity of the targets from the remaining data. The resulting data may be displayed as an image with the intensity in each region varying according to the binding affinity between targets and probes.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLE 1

Identification of DGAT Polymorphisms

The 5' region of a human DGAT gene was sequenced. This DGAT 5' flanking sequence SEQ ID NO:1 is shown in FIG. 1. The DGAT 5' flanking sequence extends from 1476 bases 5' of the transcriptional start site to a site within intron 1. The transcriptional start site is at nt (nucleotide) 1477; the translational start site is at nt 1721. This sequence was used as a reference sequence. DNA samples from various individuals were analyzed using denaturing HPLC and SSCP analysis to identify polymorphisms. These polymorphisms were confirmed by nucleotide sequence analysis.

Primers and PCR Reactions

Primers used in SSCP and HPLC analysis were as follows:

```
                                           SEQ ID NO:2
p3 primer:   5' TCAAGGACAACGGCTGCGTTGC 3';

SEQ ID NO:3
p5 primer:   5' GTCCGCTGAGGGGTGCGCTGG 3';

SEQ ID NO:4
p7 primer:   5' ACACAGAAGCCTCTTGAGTCC 3';

SEQ ID NO:5
p9 primer:   5' GTGCCCTGCGGCCCCGTCAGCCTCTC 3';

SEQ ID NO:6
p13 primer:  5' CCGCGGCTCCACGTCGGGG 3';
```

-continued
```
                                           SEQ ID NO:7
p15 primer:  5' CTGTTACAGTTGATTAGTTGC 3';

SEQ ID NO:8
p16 primer:  5' AAGAGGCTTCTGTGCATTGC 3';

SEQ ID NO:9
p17 primer:  5' CCCATGTTCTCGGACTCGGAG 3';

SEQ ID NO:10
p18 primer:  5' GTGGGGCGCACTAGGCGCTTC 3';

SEQ ID NO:11
p19 primer:  5' CCACCTCCGGGCCCTAGAC 3';
```

PCR was carried out using the following reaction conditions:

2 µl 10×buffer
0.2 µl Taq Gold DNA polymerase
0.2 µl 100×dNTP's
50 ng each primer
1–2 µl DNA template (10 to 50 ng)
0.2 µl [$^{32}$P]-α-dCTP
2 µl 100% DMSO
4 µl 50% glycerol
qc with water to 20 µl Following 35 cycles of: 1) 94° C. for 45 seconds; 2) 55° C. for 30 seconds; and 3) 72° C. for 45 seconds, PCR products were digested with restriction enzymes in appropriate restriction enzyme buffer. Restriction reactions were conducted for 2 hours to overnight. Products were resolved on 4% NuSieve agarose gels, or a sizing HPLC system. Fragment sizes were estimated by comparison with commercially available DNA fragment size standards.

SSCP Analysis

Genomic DNA from obese patients was amplified with primers p7 and p5 in a 10 µl reaction. The amplification products were digested with PvuII and PstI. Thirty µl formamide loading dye were added to each sample, the samples were heat denatured, and loaded onto a 5% polyacrylamide, 5% glycerol gel and electrophoresed for 18 hours at 4 W. The gel was then dried and exposed to x-ray film. Each lane represents one patient's amplified DNA. FIG. 2 shows the results of SSCP analysis of genomic DNA samples. The arrows indicate band shifts that represent genetic variation.

Denaturing HPLC Analysis

Figure 3A:
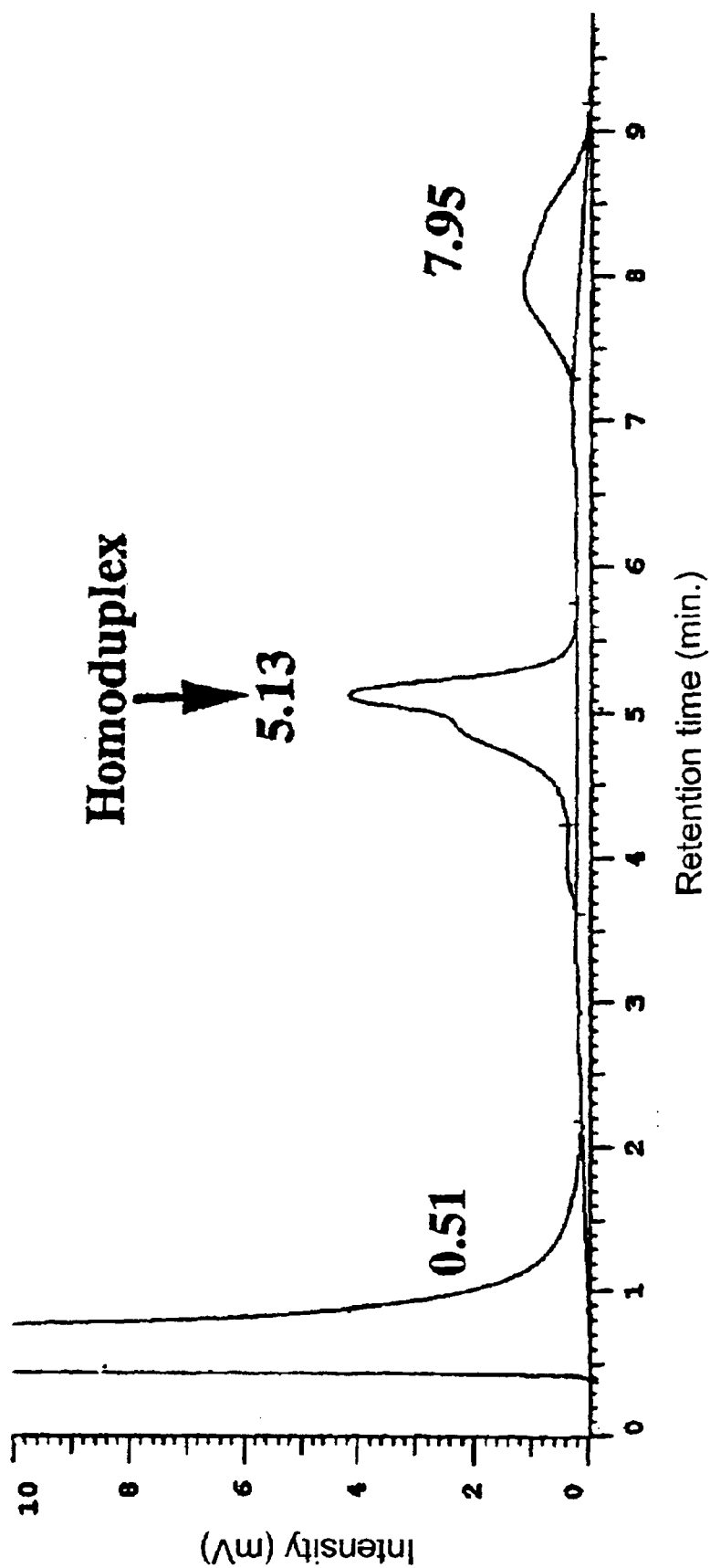
FIGS. 3A and 3B are graphs depicting DGAT promoter mutation analysis by denaturing high performance liquid chromatography.
Figure 3B:
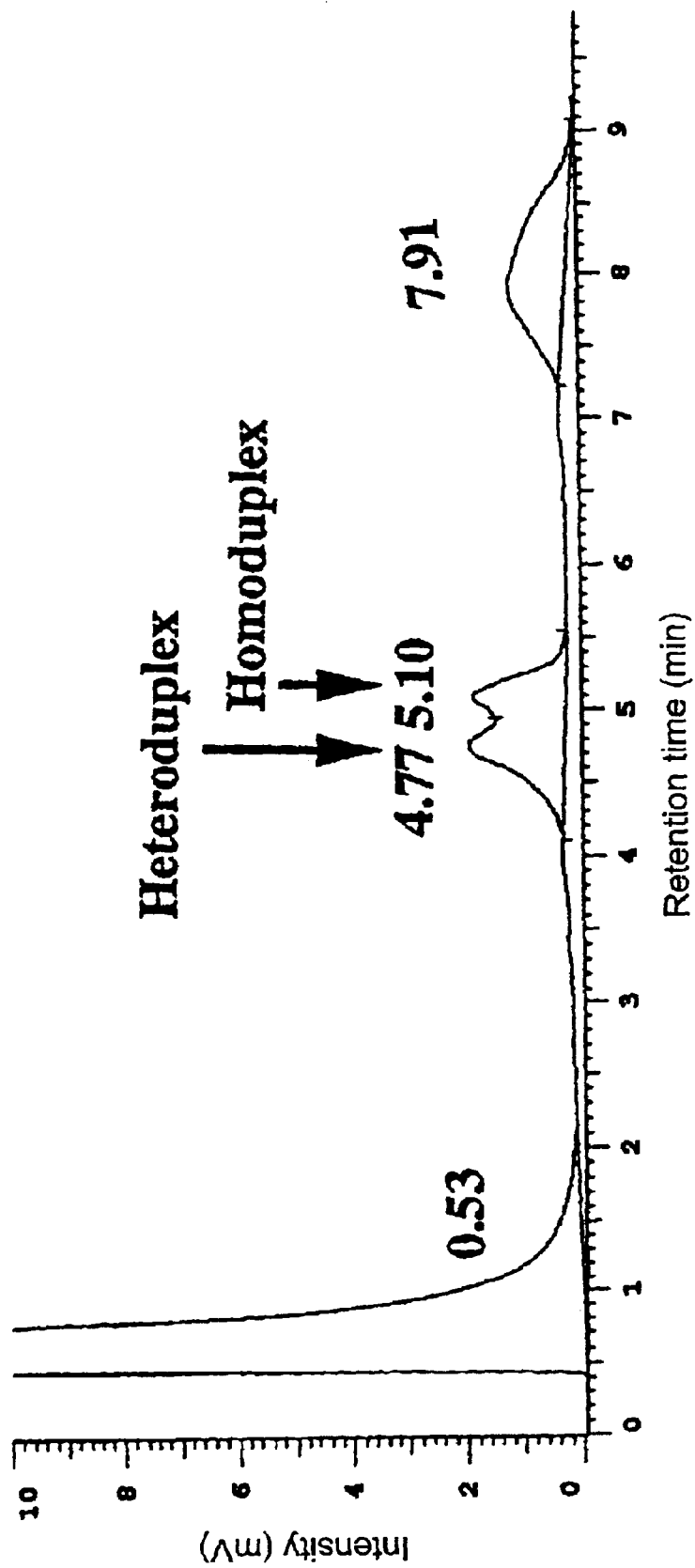

Denaturing HPLC was carried out on 574-bp amplification products of genomic DNA amplified with primers p9 and p 17. Amplification products were heat denatured, then loaded onto a Transgenomic "Wave" instrument, and separated at 67° C. with a 52–66% acetonitrile gradient. The results are shown in FIGS. 3A and 3B. Numbers next to and over peaks indicate retention times, in minutes, on the column. An A→G polymorphism at +205 relative to the transcriptional start site was detected.

Figure 4:
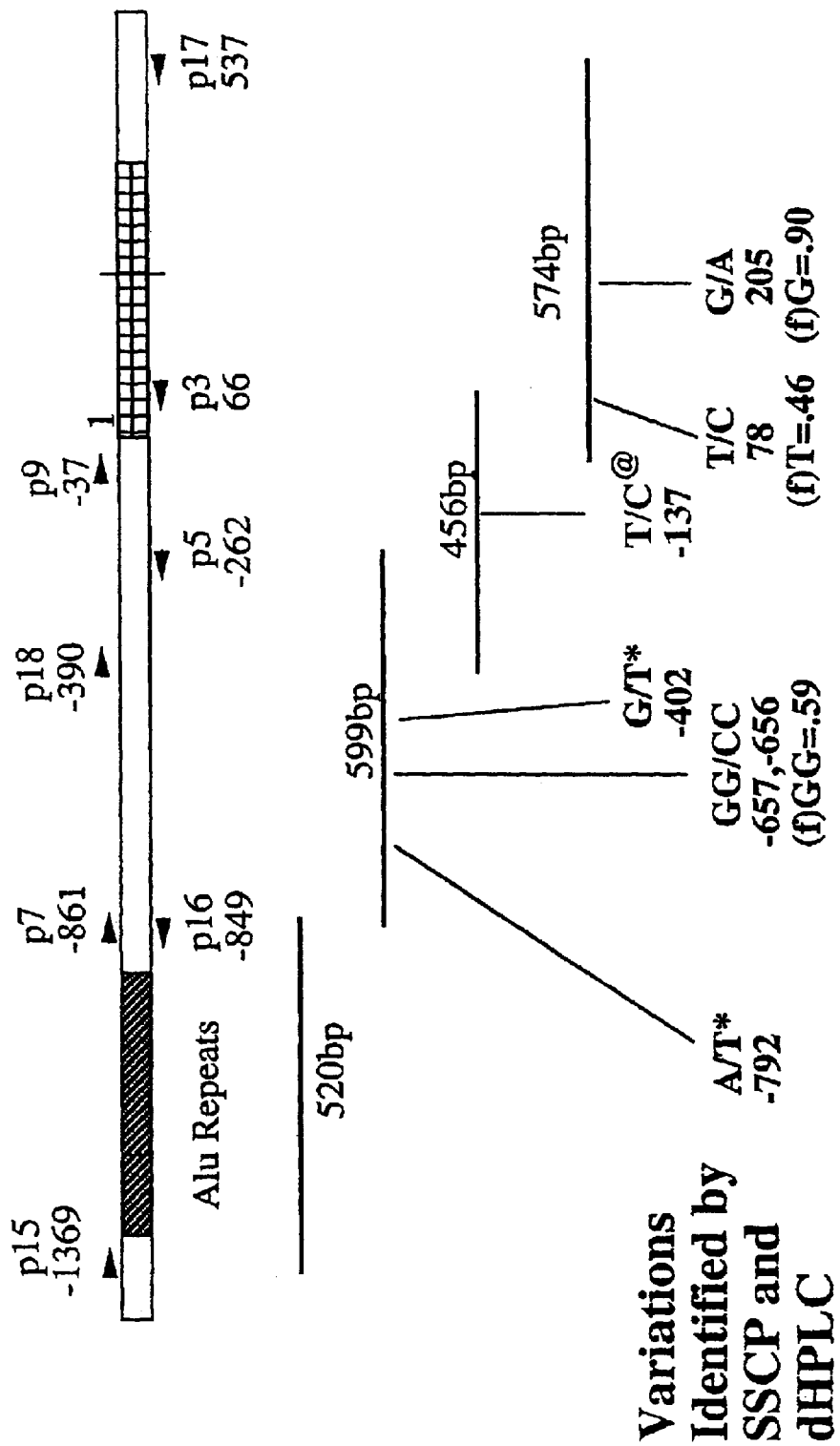
FIG. 4 depicts the amplification strategy and mutations detected in a DGAT promoter.

The above results were confirmed by DNA sequence analysis. The results are summarized in FIG. 4, which shows the amplification strategy and mutations detected in the DGAT promoter by denaturing HPLC and SSCP. Three of the variants are common: GG→CC at −656, −657; T78C; and G205A. Two of the variants are rare: A→T at −792; and G→T at −402. The T→C transition at 137 has not been examined for frequency.

EXAMPLE 2

Analysis of Occurrence of DGAT Polymorphisms in a Population

Once specific DGAT polymorphisms were identified, as described in Example 1, these polymorphisms were detected in nucleic acid samples derived from individuals, and the presence of a given polymorphism correlated with various parameters, including, diastolic blood pressure (dbp), systolic blood pressure (sbp), serum HDL levels, BMI, and total serum cholesterol levels.

The following primer pairs and restriction enzymes were used to detect the presence of specific DGAT polymorphisms:

| Variant | Primer pair | Digest PCR product with |
|---|---|---|
| T-137C | p18 + p3 | none |
| T78C and G205A | p9 + p13 or p9 + p19 | ApaI |
| G-402T | p7 + p5 | RsaI |
| GG -657, -656 CC | p7 + p5 | AciI |

Expected digestion patterns, using the above conditions, were as follows (all fragment sizes are in base pairs):

| GG -657, -656 CC | | |
|---|---|---|
| GGGG | GGCC | CCCC |
|  | 331 | 331 |
| 173 | 173 |  |
| 158 | 158 |  |
| 105 | 105 | 105 |
| 65 | 65 | 65 |
| 38 | 38 | 38 |

| G -402 T | | |
|---|---|---|
| GG | GT | TT |
| 532 | 532 |  |
|  | 461 | 461 |
|  | 71 | 71 |
| 68 | 68 | 68 |

| T78C and G205A (DNA samples amplified with p9 and p13 primers) | | | | | | | | |
|---|---|---|---|---|---|---|---|---|
| TT/AA | TT/GG | TC/GG | TC/AG | TC/AA | CC/GG | CC/AA | CC/AG | TT/AG |
| 221 | 221 | 221 | 221 | 221 |  |  |  | 221 |
| 191 |  |  | 191 | 191 | 191 |  | 191 | 191 |
|  | 146 | 146 | 146 |  | 146 | 146 | 146 | 146 |
|  |  | 134 | 134 | 134 | 134 |  | 134 |  |
|  |  |  | 87 | 87 | 87 | 87 | 87 |  |
|  | 45 | 45 | 45 |  | 45 |  | 45 | 45 |
| 18 | 18 | 18 | 18 | 18 | 18 | 18 | 18 | 18 |

| T78C (DNA samples amplified with p9 and p19 primers) | | |
|---|---|---|
| TT | TC | CC |
| 221 | 221 |  |
|  | 134 | 134 |
|  | 87 | 87 |
| 9 | 9 | 9 |

Note that all fragment sizes are approximate, and may vary by as much as ±5 bp.

The genotype and allele frequencies of the common variants in the DGAT gene, as described in Example 1, were detected in a random Turkish population and selected by gender. The results are presented in Table 1.

TABLE 1

| Genotype | | | | Allele |
|---|---|---|---|---|
| GG −656/−657 CC | | | | |
| n | GGGG | GGCC | CCCC | GG |
|  |  | All random |  |  |
| 284 | 0.37 | 0.45 | 0.18 | 0.59 |
|  |  | Males |  |  |
| 204 | 0.39 | 0.40 | 0.21 | 0.59 |
|  |  | Females |  |  |
| 80 | 0.31 | 0.56 | 0.13 | 0.59 |
| T78C | | | | |
| n | TT | TC | CC | T |
|  |  | All random |  |  |
| 439 | 0.21 | 0.50 | 0.29 | 0.46 |
|  |  | Males |  |  |
| 312 | 0.21 | 0.52 | 0.27 | 0.47 |
|  |  | Females |  |  |
| 132 | 0.19 | 0.45 | 0.36 | 0.42 |
| G205A | | | | |
| n | GG | GA | AA | G |
|  |  | All random |  |  |
| 442 | 0.79 | 0.20 | 0.01 | 0.90 |
|  |  | Males |  |  |
| 313 | 0.79 | 0.21 | 0.00 | 0.89 |
|  |  | Females |  |  |
| 133 | 0.81 | 0.18 | 0.01 | 0.91 |

The genotype and allele frequencies of the common variants were analyzed in a random Turkish population. The T78C variant was also analyzed in lean and random Turkish people; in hypotensive, random and hypertensive Turkish people; and Turkish people with low and high HDL levels.

The allele frequencies were first analyzed in a random Turkish population. An A NOVA multifactorial analysis of variables for each variation was performed. Variables analyzed were high density lipoprotein (HDL), systolic blood pressure (SBP), diastolic blood pressure (DBP), body-mass A index (BMI), age, total cholesterols, triglycerols, log transformed triglycerols, and log transformed BMI (In BMI). The data for variables in a random Turkish population associated with the DGAT T78C variation (at p<0.1) are shown in Table 2.

TABLE 2

| Variable | TT | TC | CC | Significance (P) |
|---|---|---|---|---|
| ALL | | | | |
| HDL (mg/dl) | 39.07 | 37.92 | 36.51 | 0.043 |
| SBP | 125.43 | 125.49 | 129.82 | 0.095 |
| DBP | 82.82 | 80.95 | 84.30 | 0.067 |
| BMI | 25.59 | 25.80 | 27.43 | 0.0008 |
| MALE | | | | |
| HDL (mg/dl) | 36.76 | 36.74 | 34.45 | 0.041 |
| FEMALE | | | | |
| HDL (mg/dl) | 45.42 | 41.26 | 40.26 | 0.058 |
| SBP | 127.00 | 128.47 | 137.98 | 0.026 |
| DBP | 81.00 | 80.46 | 86.91 | 0.015 |
| BMI | 25.00 | 25.84 | 28.74 | 0.003 |

Association of the G205A variant with total cholesterol and BMI was statistically associated (at p<0.1) in a random Turkish population. The data are presented in Table 3, below.

TABLE 3

| Variable | GG | GA | AA | Significance(P) |
|---|---|---|---|---|
| ALL | | | | |
| Total Cholesterol | 189 | 178 | 197 | 0.052 |
| lnBMI | 3.26 | 3.64 | 3.30 | 0.069 |
| MALE | | | | |
| Total Cholesterol | 194 | 181 | 141 | 0.038 |
| FEMALE | | | | |
| SBP | 133 | 123 | 112 | 0.017 |
| DBP | 84 | 78 | 82 | 0.020 |
| lnBMI | 3.28 | 3.20 | 3.28 | 0.074 |

The association with total cholesterol was present only with the G205A variant in all subjects and in males. The statistics represent a difference between the GG versus GA allele carriers, since only two subjects were AA carriers. The 205A allele is nearly always (>99%) linked to the 78T allele, while the 205G allele is linked to either 78T or 78C.

BMI was found to be highly significant in the initial analysis for the T78C variation in the random Turkish population. Based on this result, BMI was examined as a case control study, using the 10th and 90th percentile for BMI as the case group, and the random Turkish group minus the 10th and 90th percentile subjects for BMI as the controls. Case control studies were also performed for HDL and blood pressure. The 10% and 90% groups for HDL or BP were used as the case groups and compared to the random population.

The data presented in Table 4 suggests an association of the 78T allele with elevated HDL levels in women (p=0.023).

TABLE 4

| Variable | n | Genotype TT | TC | CC | Allele T |
|---|---|---|---|---|---|
| FEMALE | | | | | |
| <10th % HDL | 63 | 0.13 | 0.56 | 0.32 | 0.40 |
| Random with HDL > 10% | 114 | 0.21 | 0.43 | 0.36 | 0.43 |
| Random with HDL < 90% | 112 | 0.16 | 0.44 | 0.40 | 0.38 |
| >90th % HDL | 57 | 0.30 | 0.42 | 0.28 | 0.51 |
| MALE | | | | | |
| <10th % HDL | 106 | 0.17 | 0.54 | 0.29 | 0.44 |
| Random with HDL > 10% | 286 | 0.21 | 0.53 | 0.26 | 0.48 |
| Random with HDL < 90% | 269 | 0.20 | 0.51 | 0.29 | 0.46 |
| >90th % HDL | 117 | 0.19 | 0.48 | 0.33 | 0.43 |

Figure 5:
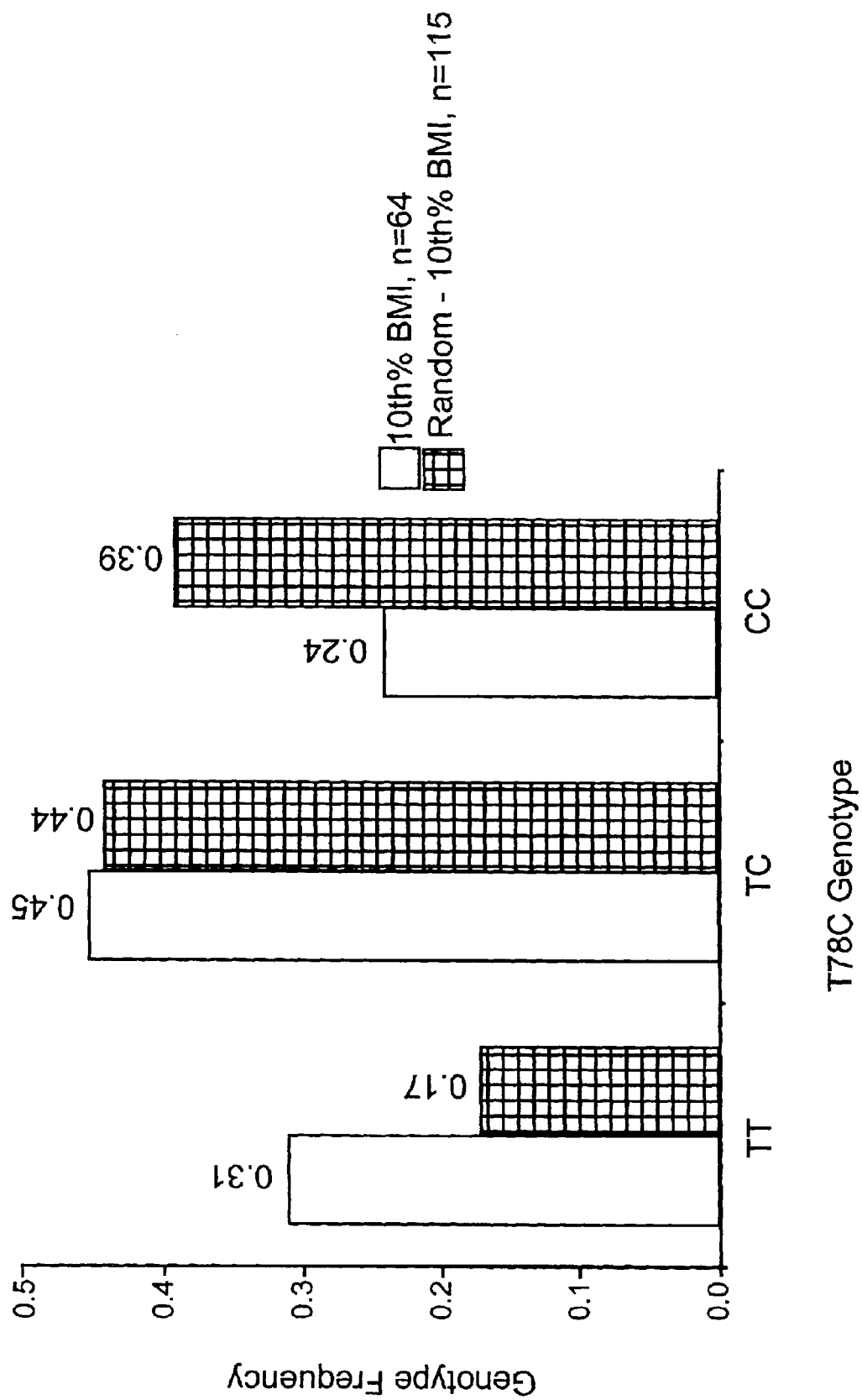
FIG. 5 is a graph depicting the distribution and frequency of the DGAT T78C polymorphism in lean versus random Turkish women.

Association of the DGAT promoter T78C variant with leanness in females and with obesity at age 25 was found to be significant. Table 5 presents data showing statistical association of the DGAT promoter T78C variation with leanness in Turkish women (compare the first 2 rows). These data are shown graphically in FIG. 5.

TABLE 5

| Variable | n | Genotype TT | TC | CC | Allele T |
|---|---|---|---|---|---|
| Females | | | | | |
| <10th % BMI | 64 | 0.31 | 0.45 | 0.24 | 0.54 |
| >10th % BMI (random) | 115 | 0.17 (P = 0.037) | 0.44 | 0.39 | 0.39 (P = 0.007) |
| <90th % BMI (random) | 116 | 0.20 | 0.47 | 0.33 | 0.47 |
| >90th % BMI | 67 | 0.21 (P = 0.17) | 0.42 | 0.37 | 0.42 (P = 0.49) |
| Males | | | | | |
| <10th % BMI (selected) | 103 | 0.19 | 0.51 | 0.30 | 0.45 |
| >10th % BMI (random) | 380 | 0.18 | 0.50 (P = 0.95) | 0.32 | 0.43 (P = 0.57) |
| <90th % BMI (random) | 364 | 0.19 | 0.52 | 0.29 | 0.45 |
| >90th% BMI (selected) | 107 | 0.17 | 0.48 (P = 0.38) | 0.35 | 0.41 (P = 0.21) |

Table 6 presents data showing association of the DGAT promoter T78C variation with obesity at age 25. The "obese" group refers to subjects selected with a BMI greater than the 90 percentile for the Turkish Heart Study (BMI=34.0 and 30.5 for females and males, respectively). The "obese at age 25" group individuals were selected from the "obese" group and also had a BMI greater than the 90th percentile at age 25.

TABLE 6

| Variable | n | Genotype TT | TC | CC | Allele T |
|---|---|---|---|---|---|
| Females | | | | | |
| Random | 129 | 0.19 | 0.45 | 0.36 | 0.42 |
| Obese | 67 | 0.21 | 0.42 | 0.37 | 0.42 |
| Obese at age 25 | 9 | 0.00 | 0.66 | 0.33 | 0.33 |
| Males | | | | | |
| Random | 313 | 0.21 | 0.52 | 0.27 | 0.47 |
| Obese | 107 | 0.17 | 0.48 | 0.35 | 0.41 |
| Obese at age 25 | 13 | 0.00 | 0.69 | 0.31 | 0.35 |

Table 7 provides data on the association of the C78T variation with blood pressure (BP) in hypotensive, random, and hypertensive Turkish women. The 10th % for BP refers to systolic or diastolic blood pressure less than 100 and 65, respectively, for females; and 104 and 66, respectively, for males. The 90th % for BP refers to systolic or diastolic blood pressure greater than 160 and 100, respectively, for females; and 150 and 98, respectively, for males.

TABLE 7

| Variable | n | Genotype | | | T |
|---|---|---|---|---|---|
| | | TT | TC | CC | |
| Female | | | | | |
| <10th % BP | 101 | 0.28 | 0.40 | 0.32 (p = 0.14) | 0.47 (p = 0.13) |
| Random | 132 | 0.19 | 0.45 | 0.36 | 0.42 |
| >90th % BP | 119 | 0.17 | 0.47 | 0.36 (p = 0.14) | 0.40 (p = 0.13) |
| Male | | | | | |
| <10th % BP | 169 | 0.23 | 0.47 | 0.30 | 0.46 |
| Random | 312 | 0.21 | 0.52 | 0.27 | 0.47 |
| >90th % BP | 170 | 0.17 | 0.54 | 0.28 | 0.44 |
| All | | | | | |
| <10th % BP | 270 | 0.25 | 0.44 | 0.31 (p = 0.06) | 0.47 (p = 0.15) |
| Random | 444 | 0.20 | 0.50 | 0.30 | 0.45 |
| >90th % BP | 289 | 0.17 | 0.51 | 0.32 (p = 0.06) | 0.43 (p = 0.15) |

These data are shown graphically in FIG. 6.

EXAMPLE 3

Transient Transfection Studies

The biological significance of the results of statistical analyses-presented in Example 2 was examined in transient cell culture expression studies. The DGAT promoter comprising either T78 or C78 was cloned into the pGL3-B vector (Promega), which contains the firefly luciferase coding sequence as the reporter. Expression of luciferase is directly proportional to the activity of the promoter regulating its transcription; thus, differences in expression of luciferase operably linked to the DGAT promoter are due to the T78C variation. In these studies, firefly luciferase expression is normalized to SV40 promoter-renilla luciferase as a standard promoter-reporter for transfection efficiency.

In one series of experiments, it was shown that less relative luciferase activity is present with the 78T DGAT promoter, compared to the DGAT promoter with C at position 78, in transient expression assays conducted in both adipocytes (34% less; p=0.011); and preadipocytes (37% less; p=0.08). These experiments were performed with various media conditions, varying the exogenous substrate. In each experiment, the T allele DGAT promoter expressed at a lower level than the C allele DGAT promoter in both adipocytes and preadipocytes. Transient transfections were also performed in HepG2 cells (a liver carcinoma line), and in CaCo2 cells (an intestinal cell line). In both HepG2 and CaCo2 cells, the DGAT promoter with T at position 78 expressed less luciferase than the DGAT promoter with C at position 78.

While the present invention has been described with reference to the specific embodiments thereof, it should be understood by those skilled in the art that various changes may be made and a equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An isolated polynucleotide comprising a polymorphism in a human diacylglycerol acyltransferase (DGAT) of SEQ ID NO: 1, wherein the polynucleotide is at least 50 nucleotides in length, and wherein the polymorphism is a T to C transition 78 bases 3' of the transcriptional start site of the DGAT of SEQ ID NO: 1.

2. The polynucleotide of claim 1, wherein the polynucleotide is coupled to a solid substrate.

3. The polynucleotide of claim 2, wherein the polynucleotide is coupled to the substrate through a linker molecule.

4. A pair of nucleic acid molecules, each from about 10 to 200 nucleotides in length, the first nucleic acid molecule of said pair comprising a sequence of at least 10 contiguous nucleotides having 100% sequence identity to the nucleic acid sequence set forth in SEQ ID NO:1 and the second nucleic acid molecule of said pair comprising a sequence of at least 10 contiguous nucleotides having 100% sequence identity to the reverse complement of the nucleic acid sequence set forth in SEQ ID NO:1, wherein said sequence of said second nucleic acid molecule is located 3' of the nucleic acid sequence of the first nucleic acid molecule in SEQ ID NO:1, and wherein the nucleic acid sequences of said first and second nucleic acid molecules are located 5' and 3', respectively, of the region of SEQ ID NO:1 corresponding to the location of a mutation associated with a diacyiglycerol acyltransferase (DGAT) polymorphism, wherein the polymorohism is located in a region of from 1476 bases 5' of the transcriptional start site to 698 bases 3' the transcriptional start site of a human DGAT of SEQ ID NO: 1.

5. The pair of claim 4, wherein the polymorphism is a T to C transition 78 bases 3' of the transcriptional start site of the DGAT gene of SEQ ID NO: 1.

6. The pair of nucleic acid molecules of claim 4, wherein the first nucleic acid molecule is detectably labeled.

7. The pair of nucleic acid molecules of claim 4, wherein the second nucleic acid molecule is detectably labeled.

8. The pair of nucleic acid molecules of claim 4, wherein the first nucleic acid molecule and the second nucleic acid molecule are detectably labeled.

9. An array of nucleic acid probes immobilized on a solid support surface, wherein said array comprises a nucleic acid probe comprising a polymorphism in a human diacyglycerol acyltransferase (DGAT) of SEQ ID NO: 1, wherein said polymorphism is associated with a condition associated with DGAT activity, wherein each nucleic acid probe is at least 30 nucleotides in length and where the polymorphism is a T to C transition 78 bases 3' of the transcriptional start site of the DGAT of SEQ ID NO: 1.

10. An isolated polynucleotide comprising a polymorphism in a human diacylglycerol acyltransferase (DGAT) of SEQ ID NO: 1, wherein said polymorphism is associated with a condition associated with DGAT activity, wherein the polynucleotide is at least 50 nucleotides in length, and wherein the polymorphism is located in a region of from 1476 bases 5' of the transcriptional start site to 698 bases 3' of the transcriptional start site of a human DGAT of SEQ ID NO: 1.

11. The polynucleotide of claim 10, wherein the polynucleotide is coupled to a solid substrate.

12. The polynucleotide of claim 11, wherein the polynucleotide is coupled to the substrate through a linker molecule.

13. An array of nucleic acid probes immobilized on a solid support surface, wherein said array comprises a nucleic acid probe comprising a polymorphism in a human diacylglycerol acyltransferase (DGAT) of SEQ ID NO: 1, wherein said polymorphism is associated with a condition associated with DGAT activity, wherein each nucleic acid probe is at least 30 nucleotides in length, and wherein the polymorphism is located in a region of from 1476 bases 5' of the transcriptional start site to 698 bases 3' of the transcriptional start site of a human DGAT of SEQ ID NO: 1.

* * * * *

SEQUENCE LISTING

```
<160> NUMBER OF SEQ ID NOS: 11

<210> SEQ ID NO 1
<211> LENGTH: 2174
<212> TYPE: DNA
<213> ORGANISM: Homo sapiens

<400> SEQUENCE: 1
tctagagtca gagtcctcag tgaaccctgg catcctgaga tccaggatgt tctcactcca      60
tgccctgtgc aatatgcaca ccaagccaag gtgggccgca actgtggctg ttacagttga     120
ttagttgctt catttaacat acaagatgtc tggggcagtg gctcatacct gtaatcccag     180
caccttcaga ggccgaggtg ggaggattgc gtgaggccag gagttcgaga ccagcctggg     240
cagaatagcg agacccccat ctttagaaaa aataacaaca ggccaggcgc ggtggcttgc     300
gcctataatc ccagcacttt gggaggccga ggtgggcgga tcacgaggtc aggagatcga     360
gaccagcctg gccaatatgg tgaaagcccg tctctactaa aaacagaaaa attagctggg     420
cgtggtggca cgcgcctgta gtcctggcta ctcgggaggc tgaggcagga gaatcgcttg     480
aacccaggag gtggaggttg cagtgagacg agatcgcgct actgcactcc agcctggcga     540
cagagtgaga ctgtctcaaa aaaagaaaaa agaaaacaaa aaacaacagg gcggttgcac     600
```

```
aggccgtgca aatgcacaga agcctcttga gtcccggcga tccagcggcc cagacttctg      660
acatcctgga gaggctggcc cacgatggaa actgggaggc cctgagagtt gagggacgtg      720
gagctccttg tggagagagt gggtgggctg agaagacacc accaaggggc ctgcgccctc      780
gccctcgccc tcgccctcct ctcgccgggc tctgcaggcg gggaggtgga gagcctggga      840
gtcgcgtgca aggcaggcgt cccggtgacg cagggcctgg tgcatttctc cagcttggtc      900
ttctgacctg gcccttgtct gacgtccccc taaggcgaag aaaagcaggt tcctgccggg      960
gtaaccagag ggctcgcgga gcagaagcgc gccaggggacg ttactgtaag ctgcgtgcgc     1020
agaaaccaac gcgctgggtg gcgggcgacg cgagccgccg cggacaccgg cccggacagc     1080
tggaccgtgg cgcactaggc gcttcctaaa tgattgcccg gagtgactcg ccgagacccc     1140
gtgtgtacac aagtgggacg aggggcgggc gcacagcggc caggaagtcg gggcccagcg     1200 caccctcag cggaccatcc cgctccgtgg ggccggacag gaccccggga ccacgcggga      1260
gcgatgcaag gtccgttccc gctgcgcgca cttgcggccc gcagcccggg ccctgggagc     1320
tgccacggct cccagggtgt tctgcgccgg tgcggccgcg gcgactacga ctcccagggt     1380
gctctgcgcc ggcgcgcccg cggcgactac gactcccagg gtgccctgcg ccccgtcagc     1440
ctctccaggc cccgcctcag gtcggccgcg gactacaaat ggacgagaga ggcggccgtc     1500
cattagttag cggctccgga gcaacgcagc cgttgtcctt gaggccgacg ggcctgacgc     1560
gggcgggttg aacgcgctgg tgaggcggtc acccgggcta cggcggccgg caggggggcag    1620 tggcggccgt tgtctagggc ccggaggtgg ggccgcgcgc ctcgggcgct acgaacccgg     1680
caggcccacg cttggctgcg gccgggtgcg ggctgaggcc atgggcgacc gcggcagctc     1740
ccggcgccgg aggacagggt cgcggccctc gagccacggc ggcggcgggc ctgcggcggc     1800
ggaagaggag gtgcgggacg ccgctgcggg ccccgacgtg ggagccgcgg gggacgcgcc     1860
agccccggcc cccaacaagg acggagacgc cggcgtgggc agcggccact gggagctgag     1920
gtagcggagc gcctgacccc ctaacctctg acccaagggc cccgcgactt tccggggttg     1980
gccgaagcgc gagctccgag tccgagaaca tgggccctgg gctaagcggg gatcggtgtg     2040
ccctatgggc cctgtgggga aactgaggct tggggagagt cacctgacaa ggtcactggg     2100 tagggggctct ggactgcctt gccaggcaga ggggagccgg caggtgtccg catccagatc    2160
ctcttggtct gtgc                                                        2174

<210> SEQ ID NO 2
<211> LENGTH: 22
<212> TYPE: DNA
<213> ORGANISM: Artificial Sequence
<220> FEATURE:
<223> OTHER INFORMATION: p3 primer

<400> SEQUENCE: 2
tcaaggacaa cggctgcgtt gc                                                22

<210> SEQ ID NO 3
<211> LENGTH: 21
<212> TYPE: DNA
<213> ORGANISM: Artificial Sequence
<220> FEATURE:
<223> OTHER INFORMATION: p5 primer

<400> SEQUENCE: 3
gtccgctgag gggtgcgctg g                                                 21
```

<210> SEQ ID NO 4
<211> LENGTH: 21
<212> TYPE: DNA
<213> ORGANISM: Artificial Sequence
<220> FEATURE:
<223> OTHER INFORMATION: p7 primer

<400> SEQUENCE: 4
acacagaagc ctcttgagtc c                                              21

<210> SEQ ID NO 5
<211> LENGTH: 26
<212> TYPE: DNA
<213> ORGANISM: Artificial Sequence
<220> FEATURE:
<223> OTHER INFORMATION: p9 primer

<400> SEQUENCE: 5
gtgccctgcg gccccgtcag cctctc                                         26

<210> SEQ ID NO 6
<211> LENGTH: 19
<212> TYPE: DNA
<213> ORGANISM: Artificial Sequence
<220> FEATURE:
<223> OTHER INFORMATION: p13 primer

<400> SEQUENCE: 6
ccgcggctcc acgtcgggg                                                 19

<210> SEQ ID NO 7
<211> LENGTH: 21
<212> TYPE: DNA
<213> ORGANISM: Artificial Sequence
<220> FEATURE:
<223> OTHER INFORMATION: p15 primer

<400> SEQUENCE: 7
ctgttacagt tgattagttg c                                              21

<210> SEQ ID NO 8
<211> LENGTH: 20
<212> TYPE: DNA
<213> ORGANISM: Artificial Sequence
<220> FEATURE:
<223> OTHER INFORMATION: p16 primer

<400> SEQUENCE: 8
aagaggcttc tgtgcattgc                                                20

<210> SEQ ID NO 9
<211> LENGTH: 21
<212> TYPE: DNA
<213> ORGANISM: Artificial Sequence
<220> FEATURE:
<223> OTHER INFORMATION: p17 primer

<400> SEQUENCE: 9
cccatgttct cggactcgga g                                              21

<210> SEQ ID NO 10
<211> LENGTH: 21
<212> TYPE: DNA
<213> ORGANISM: Artificial Sequence
<220> FEATURE:
<223> OTHER INFORMATION: p18 primer

```
<400> SEQUENCE: 10
gtggggcgca ctaggcgctt c                                              21

<210> SEQ ID NO 11
<211> LENGTH: 19
<212> TYPE: DNA
<213> ORGANISM: Artificial Sequence
<220> FEATURE:
<223> OTHER INFORMATION: p19 primer

<400> SEQUENCE: 11
ccacctccgg gccctagac                                                 19
```